(12) United States Patent
Govindaraj et al.

(10) Patent No.: US 12,261,451 B2
(45) Date of Patent: Mar. 25, 2025

(54) SYSTEMS AND METHODS FOR SEALING AND PROVIDING WIRELESS POWER TO WEARABLE OR IMPLANTABLE DEVICES

(71) Applicant: Verily Life Sciences LLC, South San Francisco, CA (US)

(72) Inventors: Arvind Govindaraj, Mountain View, CA (US); David Lari, San Francisco, CA (US); Cindy Au, Redwood City, CA (US)

(73) Assignee: VERILY LIFE SCIENCES LLC, Dallas, TX (US)

( * ) Notice: Subject to any disclaimer, the term of this patent is extended or adjusted under 35 U.S.C. 154(b) by 0 days.

(21) Appl. No.: 17/624,465

(22) PCT Filed: Jul. 2, 2020

(86) PCT No.: PCT/US2020/040666
§ 371 (c)(1),
(2) Date: Jan. 3, 2022

(87) PCT Pub. No.: WO2021/003370
PCT Pub. Date: Jan. 7, 2021

(65) Prior Publication Data
US 2022/0360109 A1    Nov. 10, 2022

Related U.S. Application Data

(60) Provisional application No. 63/004,856, filed on Apr. 3, 2020, provisional application No. 62/870,136, filed on Jul. 3, 2019.

(51) Int. Cl.
*H02J 50/10* (2016.01)
*H02J 50/60* (2016.01)
*H02J 50/80* (2016.01)

(52) U.S. Cl.
CPC .............. *H02J 50/10* (2016.02); *H02J 50/60* (2016.02); *H02J 50/80* (2016.02)

(58) Field of Classification Search
CPC .. H02J 50/10; H02J 50/12; H02J 50/20; H02J 50/60; H02J 50/80; H04B 5/0031;
(Continued)

(56) References Cited

U.S. PATENT DOCUMENTS

2010/0244578 A1* 9/2010 Yoshikawa ............. H02J 50/90
                                                                                   307/104
2011/0263953 A1    10/2011 Markle et al.
(Continued)

FOREIGN PATENT DOCUMENTS

CN        101321494 A    12/2008
CN        101652094 A    2/2010
(Continued)

OTHER PUBLICATIONS

International Application No. PCT/US2020/040666, International Search Report and Written Opinion, mailed Oct. 26, 2020, 15 pages.
(Continued)

*Primary Examiner* — Levi Gannon
(74) *Attorney, Agent, or Firm* — Kilpatrick Townsend & Stockton LLP

(57) ABSTRACT

One example device includes a first housing portion defining a first coupling surface; a second housing portion defining a second coupling surface, the first housing portion coupled to the second housing portion to form a housing, the first housing portion and the second housing portion defining an opening, the opening intersecting the first coupling surface and the second coupling surface; a first gasket positioned between the first coupling surface and the second coupling surface, the first gasket providing a first seal between the
(Continued)

first housing portion and the second housing portion, a printed circuit board ("PCB") disposed within the housing and coupled to at least one of the first or second housing portions; an electrical connector electrically coupled to the printed circuit board and positioned within the opening; and a second gasket positioned between the electrical connector and the housing, the second gasket providing a second seal between the electrical connector and the housing, wherein the first gasket is positioned to abut the second gasket and wherein compression of the first gasket between the first and second housing portions provides a third seal between the first gasket and the second gasket. Another example device includes a wireless field driver comprising a first antenna coil and an electrical current source electrically coupled to the first antenna coil; an electromagnetic field ("EMF") sensor comprising a second antenna coil, wherein the EMF sensor is configured to generate a sensor signal indicative of a signal strength from the first antenna coil; a non-transitory computer-readable medium; and a processor in communication with the non-transitory computer-readable medium, the processor configured to execute processor-executable instructions stored in the non-transitory computer-readable medium to: cause the electrical current source to output a current to the first antenna coil to generate a first EMF; estimate the signal strength of the first EMF based on the sensor signal; and adjust the current to the first antenna coil based on an estimated signal strength of the first EMF to maintain a power characteristic and generate a second EMF at the first antenna coil.

22 Claims, 21 Drawing Sheets

(58) Field of Classification Search
CPC .. H04B 5/0037; H04B 5/0043; H04B 5/0075; H04B 5/0081; H04B 5/0087; H04B 5/0093
See application file for complete search history.

(56) References Cited

U.S. PATENT DOCUMENTS

| | | |
|---|---|---|
| 2012/0248887 A1 | 10/2012 | Kesler et al. |
| 2012/0291254 A1 | 11/2012 | Say |
| 2013/0057078 A1 | 3/2013 | Lee et al. |
| 2013/0062965 A1* | 3/2013 | Chernokalov .......... H02J 50/10 307/104 |
| 2014/0071571 A1* | 3/2014 | Tseng ..................... H02H 3/20 361/91.1 |
| 2014/0111019 A1 | 4/2014 | Roy et al. |
| 2014/0333146 A1 | 11/2014 | Dibben et al. |
| 2015/0180593 A1* | 6/2015 | Hamilton ............. H04B 17/318 455/107 |
| 2015/0364929 A1 | 12/2015 | Davis |
| 2016/0043566 A1* | 2/2016 | Terao .................... H02J 7/0047 307/104 |
| 2016/0084894 A1* | 3/2016 | Govindaraj ........... G01R 25/04 327/236 |
| 2016/0099578 A1* | 4/2016 | Hwang ..................... H02J 7/00 307/104 |
| 2016/0238731 A1* | 8/2016 | Chopra .................. G01V 3/101 |
| 2016/0270700 A1 | 9/2016 | Baxi et al. |
| 2017/0237296 A1* | 8/2017 | Keith .................. H02J 7/00714 307/104 |
| 2017/0290546 A1 | 10/2017 | Antonio et al. |
| 2017/0361114 A1* | 12/2017 | Aghassian ............ A61N 1/3787 |
| 2017/0361116 A1 | 12/2017 | Aghassian et al. |
| 2018/0146895 A1 | 5/2018 | Biederman et al. |
| 2020/0177029 A1* | 6/2020 | Homma ................. H01Q 3/267 |
| 2020/0389061 A1* | 12/2020 | Lee ......................... H02J 50/80 |

FOREIGN PATENT DOCUMENTS

| | | |
|---|---|---|
| CN | 107278137 A | 10/2017 |
| CN | 207651709 U | 7/2018 |
| EP | 2256895 | 12/2010 |

OTHER PUBLICATIONS

International Application No. PCT/US2020/040666, Invitation to Pay Additional Fees and, Where Applicable, Protest Fee, mailed Aug. 21, 2020, 2 pages.

Abatti et al., "Analysis and Optimisation of Three-coil Wireless Power Transfer Systems", IET Power Electronics, vol. 11, No. 1, Jan. 2018, pp. 68-72.

European Application No. 20835436.5 , "Extended European Search Report", Jun. 23, 2023, 10 pages.

Chinese Application No. 202080048605.1 , "Office Action", Jun. 24, 2024, 6 pages.

* cited by examiner

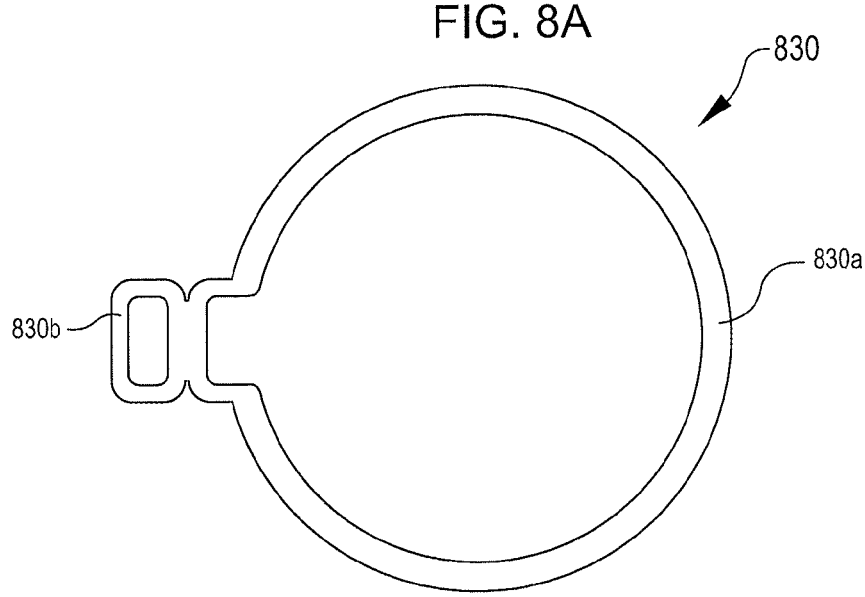
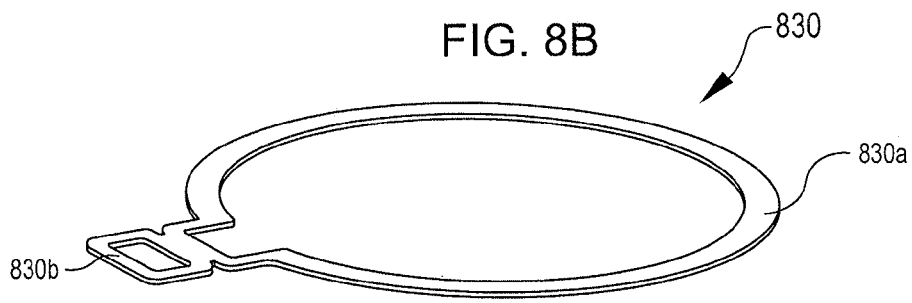
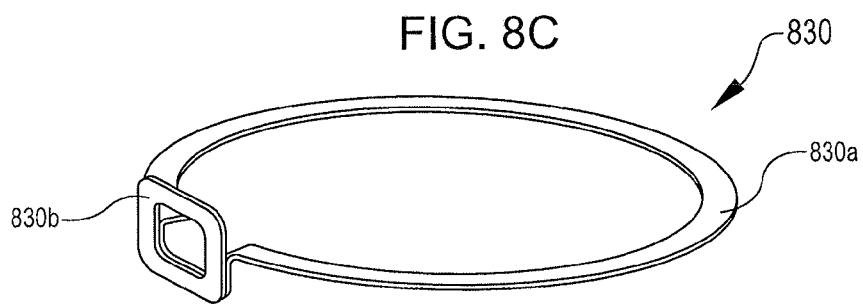

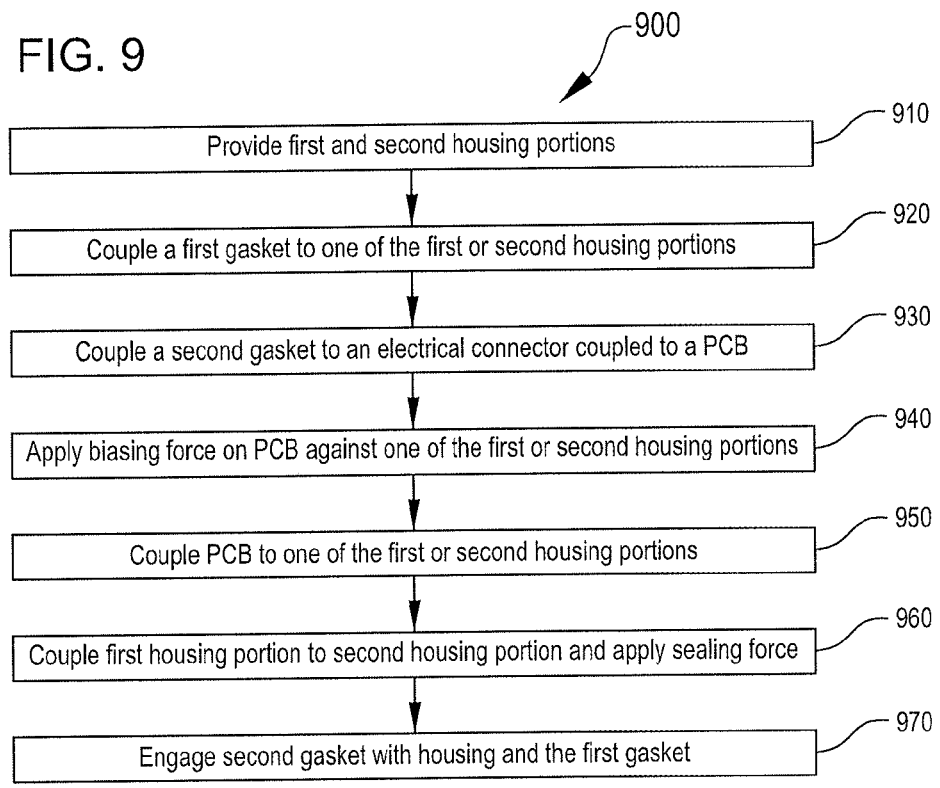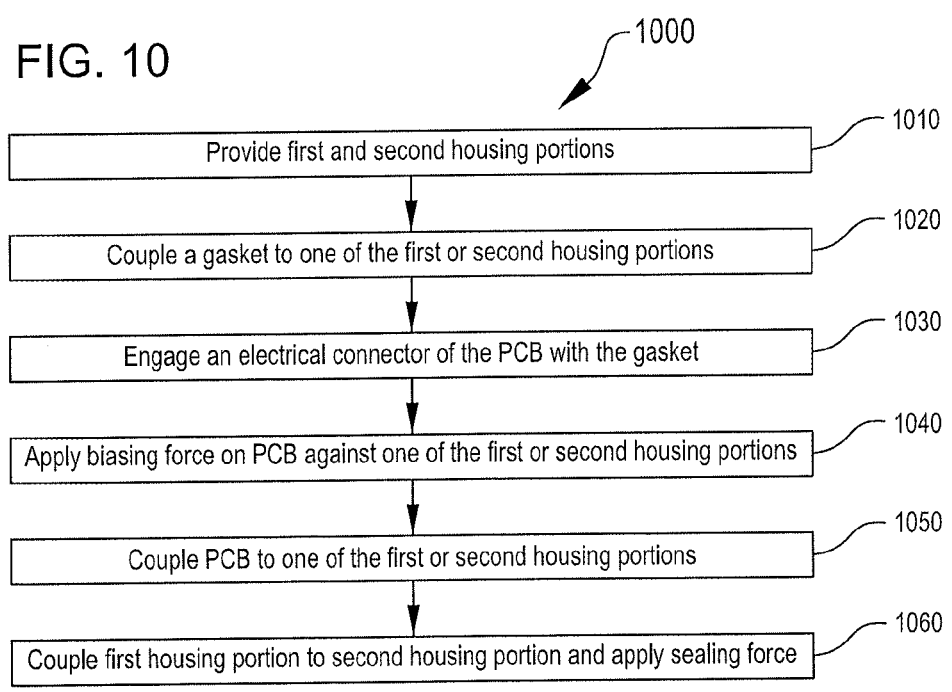

SYSTEMS AND METHODS FOR SEALING AND PROVIDING WIRELESS POWER TO WEARABLE OR IMPLANTABLE DEVICES

FIELD

The present application generally relates to wearable devices and near-field wireless power transmission, and more specifically relates to systems and methods for sealing wearable electronic devices and dynamic control of near-field wireless power.

BACKGROUND

Wearable electronic devices may be used for a variety of reasons. For example, wristwatches, activity monitors, physiological sensors, etc. may be worn to provide information to the wearer or to sense characteristics of the wearer. Sensed information may be viewed by the wearer or may be transmitted to another device, such as the wearer's smartphone. Further, wearable or implantable electronic devices typically derive power from an on-board battery; however, it is also possible to wirelessly transmit power to such devices. Wireless power transmission may be used to power the electronic device or to charge an on-board battery. Such systems generate an electromagnetic coupling between an antenna in a charger device and an antenna in the target device to transfer power from the charger to the target device.

SUMMARY

Various examples are described for sealing and providing wireless power to wearable or implantable devices. One example device includes a first housing portion defining a first coupling surface; a second housing portion defining a second coupling surface, the first housing portion coupled to the second housing portion to form a housing, the first housing portion and the second housing portion defining an opening, the opening intersecting the first coupling surface and the second coupling surface; a first gasket positioned between the first coupling surface and the second coupling surface, the first gasket providing a first seal between the first housing portion and the second housing portion, a printed circuit board ("PCB") disposed within the housing and coupled to at least one of the first or second housing portions; an electrical connector electrically coupled to the printed circuit board and positioned within the opening; and a second gasket positioned between the electrical connector and the housing, the second gasket providing a second seal between the electrical connector and the housing, wherein the first gasket is positioned to abut the second gasket and wherein compression of the first gasket between the first and second housing portions provides a third seal between the first gasket and the second gasket.

Another example device includes a first housing portion defining a first coupling surface; a second housing portion defining a second coupling surface, the first housing portion coupled to the second housing portion to form a housing, the first housing portion and the second housing portion defining an opening, the opening intersecting the first coupling surface and the second coupling surface; a printed circuit board ("PCB") disposed within the housing and coupled to at least one of the first or second housing portions; an electrical connector electrically coupled to the printed circuit board and positioned within the opening; a gasket defined to correspond to the first and second coupling surfaces and to the electrical connector; and wherein: the gasket is positioned between the first coupling surface and the second coupling surface, the gasket providing a first seal between the first housing portion and the second housing portion, and the electrical connector is positioned to extend through the gasket, the gasket providing a second seal between the electrical connector and the housing.

One example method includes providing a first housing portion defining a first coupling surface; providing a second housing portion defining a second coupling surface, the first and second housing portions defining a housing when coupled, the housing defining an opening, the opening intersecting the first coupling surface and the second coupling surface; physically coupling a first gasket to one of the first or second coupling surfaces; providing a printed circuit board ("PCB") having an electrical connector; physically coupling a second gasket to the electrical connector; physically coupling the PCB to at least one of the first or second housing portions and engaging the second gasket with the at least one of the first or second housing portions; physically coupling the one of the first or second housing portions to the other of the first or second housing portions; applying a sealing force to the first and second housing portions to compress the first gasket to create a first seal; engaging the second gasket with the other of the first or second housing portions to create a second seal; and engaging the second gasket with the first gasket to create a third seal.

Another example method includes providing a first housing portion defining a first coupling surface; providing a second housing portion defining a second coupling surface, the first and second housing portions defining a housing when coupled, the housing defining an opening, the opening intersecting the first coupling surface and the second coupling surface; providing a printed circuit board ("PCB") having an electrical connector; physically coupling the PCB to at least one of the first or second housing portions; physically coupling a gasket to one of the first or second coupling surfaces; engaging the gasket with the one of the first or second housing portions and the electrical connector; physically coupling the one of the first or second housing portions to the other of the first or second housing portions; and applying a sealing force to the first and second housing portions to compress the gasket to create a first seal, and where the electrical connector is positioned to extend through the gasket, the gasket providing a second seal between the electrical connector and the housing.

Another example device includes a wireless field driver comprising a first antenna coil and an electrical current source electrically coupled to the first antenna coil; an electromagnetic field ("EMF") sensor comprising a second antenna coil, wherein the EMF sensor is configured to generate a sensor signal indicative of a signal strength from the first antenna coil; a non-transitory computer-readable medium; and a processor in communication with the non-transitory computer-readable medium, the processor configured to execute processor-executable instructions stored in the non-transitory computer-readable medium to: cause the electrical current source to output a current to the first antenna coil to generate a first EMF; estimate the signal strength of the first EMF based on the sensor signal; and adjust the current to the first antenna coil based on an estimated signal strength of the first EMF to maintain a power characteristic and generate a second EMF at the first antenna coil.

One example method includes causing an electrical current source of a wireless field driver of a wireless device to output a current to a first antenna coil to generate a first EMF; receiving one or more signals from an EMF sensor of the wireless device indicating a sensed strength of the first EMF, the EMF sensor comprising a second antenna coil; estimating a strength of the first EMF based on the one or more sensor signals; and adjusting the current based on the estimated strength of the first EMF to generate a second EMF at the first antenna coil.

One example non-transitory computer-readable medium comprises processor-executable instructions to cause a processor to cause an electrical current source of a wireless field driver of a wireless device to output a current to a first antenna coil to generate a first EMF; receive one or more signals from an electromagnetic field ("EMF") sensor indicating a sensed strength of the first EMF, the EMF sensor comprising a second antenna coil; determine a strength of the first EMF based on the one or more signals; and adjust the current based on the sensed strength of the first EMF to generate a second EMF.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 8A-8C show an example sealing component;

FIGS. 9-10 show example methods for sealing wearable electronic devices;

DETAILED DESCRIPTION

Figure 1A:
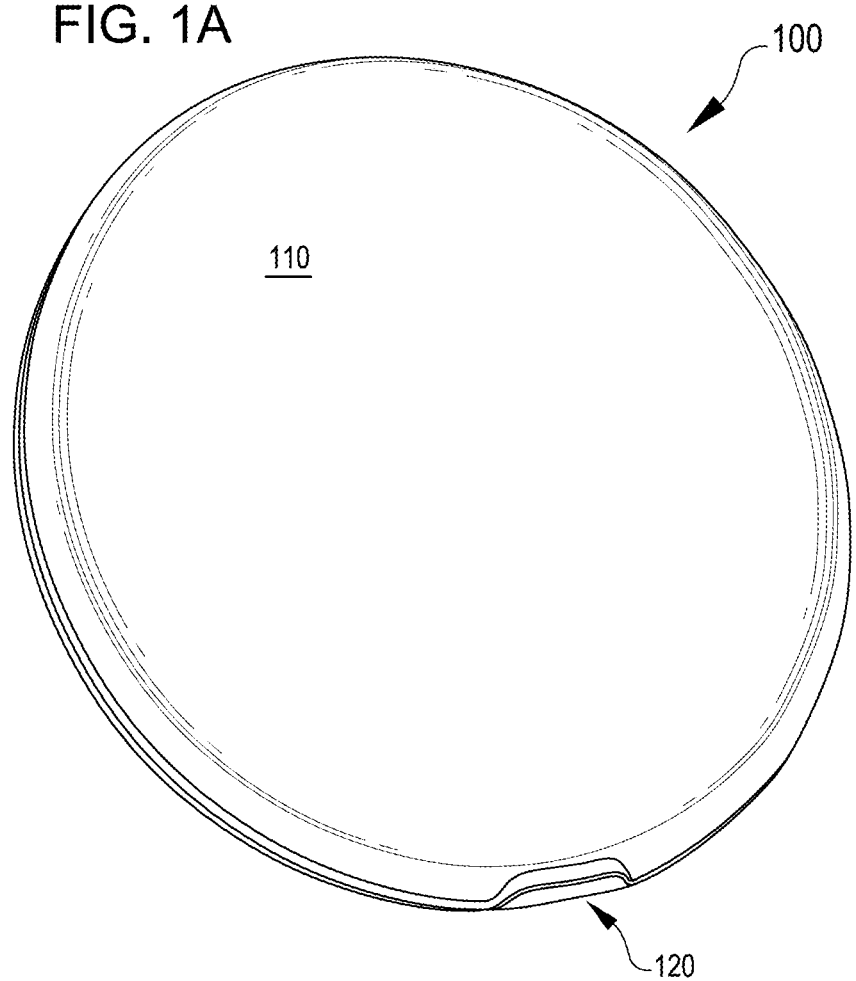
FIGS. 1A-1B show an example wearable device and electric charging port.

Examples are described herein in the context of systems and methods for sealing and providing wireless power to wearable or implantable devices. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Some electronic devices may be worn against the user's skin or on the user's body and may be subjected to many different types of materials that may damage or destroy sensitive electronics within the wearable device. Because wearable devices may have a relatively long useful life, e.g., multiple years, it is likely that the device will encounter many different environments. In addition, the user may occasionally clean the device, which may include rinsing the device under a faucet or wearing it into the shower or a bath. Thus, these devices may be sealed during assembly to prevent ingress of such materials, notably moisture.

An illustrative example of such a device has two halves of a mechanical housing that contain and protect the device's electronics. The two halves of the housing are pressed together and sealed during manufacture to protect the electronics. The seal in this example is a gasket that matches the perimeters of the two halves of the housing and sits between the two housing halves when they are fastened together, such as using screws or a pressure-sensitive adhesive ("PSA"). During this process, the gasket is compressed between the two housing halves and seals the assembled housing.

However, example wearable devices according to this disclosure may include one or more ports to enable cables or wires to be connected to the wearable device. In this example, the wearable device has an electrical charging port to enable a charging cable to be connected to the device to charge the device's battery. Thus, the perimeter of the assembled housing is interrupted by an opening to accommodate the charging port. The opening in this example is oriented perpendicularly to the gasket that seals the two housing halves, and thus, the gasket cannot seal the entire perimeter of the housing.

Instead, this opening is sealed with a second gasket that is pressed against the connector assembly that is positioned within the opening. The connector assembly includes a connector cover and an electrical connector. The electrical connector provides the connection point for a charging cable, and is also electrically connected to a printed circuit board ("PCB") mounted to one of the two halves of the housing. To compress the second gasket, the second gasket is positioned between the connector cover and the housing. The PCB is biased against the outer edge of the housing, which in turn presses the connector cover against the housing. The PCB is then securely attached to one of the housing halves to maintain the biasing force. The main or "perimeter" gasket, discussed above, is then compressed between the two housing halves and against the second or "opening" gasket to both seal the housing halves and to form a seal at the interface of the two gaskets. Thus, two gaskets together provide a complete seal to prevent moisture and contaminant ingress into the wearable device.

This example device employs a connector opening that straddles the joint between the two housing halves, thereby creating a need to seal the housing halves together as well as simultaneously seal the connector opening. However, because the planes in which the seals lie are orthogonal to each other, it creates a problem in that the perimeter gasket used to seal the two housing halves together cannot extend through the opening and thus cannot seal the opening. In addition, because the two different gaskets interface, ensuring a tight seal between the two gaskets must be accomplished by compressive forces on each gasket. An advantage of using gaskets to seal the two housing portions and the electrical connector, rather than welding or otherwise fusing the two housing portions together to seal the wearable device, is that the device may be re-opened to fix or replace components, such as a battery, and then re-sealed. Further, manufacturing and assembly processes may be simplified by using gaskets rather than more complex processes, such as welding, epoxying, or otherwise fusing the two halves together.

To power or charge an implanted electronic device, a user may bring a charger device within proximity of the implanted device and activate the charging functionality, such as by pressing a button or interacting with a touch screen. The charger device then activates a power amplifier and sends an alternating current having a predetermined frequency through a transmit antenna coil to generate an alternating electromagnetic field ("EMF"). A corresponding receive antenna coil in the implanted device couples with the EMF and obtains electromagnetic ("EM") energy from the field, which it then uses to power various electronic components or to charge its battery.

However, the power received by the implanted device may vary based on the strength of the EMF or the quality of the coupling with the EMF, which may change based on the relative positioning of the antenna coils, e.g., the alignment of the antenna coils or the distance between the coils. Thus, the amount of power received by the implant device may vary. In addition, if the target device is not able to send feedback information to the charger device, the charge device still needs to ensure that an appropriate amount of EMF is transmitted. In this example, to help the charger device output an EMF with a target power level, the charger device includes an integrated EMF sensor.

The EMF sensor in this example includes a second antennal coil that is aligned coaxially with the transmit antenna coil. This second coil also electromagnetically couples with the EMF and outputs a signal based on the strength of the EMF. The signal from the second antenna coil is sent both to a peak detector and to a phase detector. The peak detector receives the signal and outputs a DC value indicating the peak voltage (or current) output by the second antennal coil. The phase detector receives the signal from the second antenna coil and outputs a phase change based on a reference signal.

The peak voltage (or current) signal and the phase change signal are both transmitted to a microcontroller, which receives the signals and determines the strength of the EMF based on the peak voltage (or current) signal. The phase change signal is used to indicate the RF load impedance or to receive near-field communications from the target device, e.g., an amount of power received from the EMF by the target device. Based on the estimated EMF strength and a target EMF strength, the microcontroller executes a proportional-integral-derivative ("PID") feedback control loop to adjust the amount of current output by the power amplifier to achieve the target EMF strength. Thus, the charger device may be able to dynamically adjust the strength of the generated EMF in real-time or near-real time to provide the power needed by the target device.

In addition to estimating the EMF strength and obtaining RF load information, such an EMF sensor can enable other functionality, such as foreign object detection, power amplifier tuning to improve efficiency, and mitigation of electromagnetic interference ("EMI"). For example, the receive antenna coil in a target device typically introduces harmonic oscillations into the generated EMF, whereas an interfering foreign object typically will not. Thus, by filtering the signal received from the EMF sensor to identify harmonics, or by identifying a lack of such harmonics, foreign objects may be detected. Alternatively, foreign objects may be detected instead (or in addition) based on a determined RF load impedance exceeding a threshold impedance. In addition, EMI mitigation may be employed based on the magnitude of the sensed harmonics. Such harmonics typically correlate with EMI, and so if the magnitude of one or more sensed harmonics exceeds a threshold, the EMF strength may be reduced to reduce potential EMI effects.

Further, power amplifier efficiency may also be improved by adjusting a duty cycle of the power amplifier based on the detected EMF. To do so, the the transmit current is held constant, the duty cycle is varied, and the power usage at each tested duty cycle is determined. A duty cycle may then be selected by identifying the lowest calculated power usage across the tested duty cycles.

Thus, such an example charger may be able to adjust its own power output in real-time to ensure an appropriate amount of energy is output to a target device. Further, such techniques enable the use of less sophisticated target devices, such as target devices that lack separate communications capability, e.g., by omitting Bluetooth ("BT") or BT low-energy ("BLE") components. In addition, still other advantages, such as foreign object detection, load impedance detection and power amplifier tuning, and EMI mitigation, may be realized according to some examples.

These illustrative examples are given to introduce the reader to the general subject matter discussed herein and the disclosure is not limited to this example. The following sections describe various additional non-limiting examples and examples of systems and methods for sealing and providing wireless power to wearable or implantable devices.

Figure 1B:
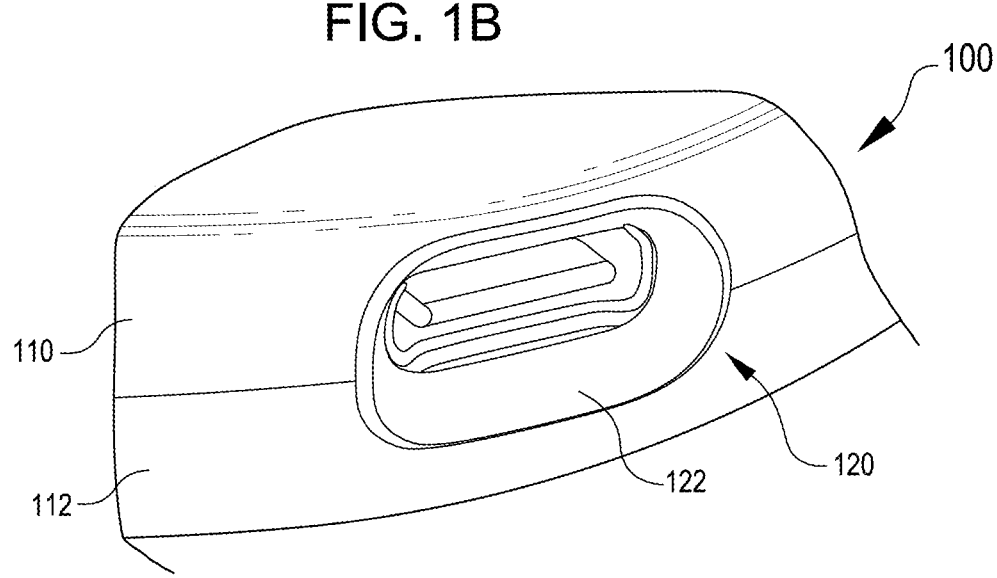

Referring now to FIGS. 1A-1B, FIGS. 1A-1B show an example wearable electronic device 100. The device 100 may be any suitable electronic device and may provide any of a variety of functionalities to the user. For example, the device 100 in this example is used to wirelessly charge or otherwise wirelessly supply power to implanted devices within the wearer; however, other types of wearable devices may include sensors, such as pulse monitors, accelerometers, electrocardiogram electrodes, etc., or may be user devices such as a smartwatch, a personal communication device (e.g., an emergency communications device for elderly users), headphones, earbuds, etc.

Because the device is intended to be worn by a user and to be used over an extended period of time, e.g., weeks, months, or years, it will be subjected to various environmental conditions that might damage the electronic components within the device, such as moisture or running water. To prevent such damage, the device is sealed to prevent moisture ingress.

As can be seen, the wearable device 100 has a housing that is made by coupling and sealing two housing portions 110, 112 together. In this example, the device is generally disc-shaped with two housing portions 110, 112 that seal along a circular perimeter. It should be appreciated that any suitable device shape may be used, however. This perimeter is interrupted by an opening with an electrical connector 120 that can be used to connect an external device, such as an electric charger or a computing device, to charge the device 100 or to communicate with the device 100.

Because the device's housing includes an electrical connector 120 that interrupts the interface between the housing portions 110, 112, a simple circumferential seal between the two housing portions 110, 112 will not entirely seal the device 100. Further, because the wearable device is intended to be used for a period of weeks, months, or years, it may need to be repaired or have components replaced, such as a battery, and so the device may need to be opened. As a result, a permanent seal, such as a weld or epoxy adhesive, may not be desirable. Instead, as will be discussed in more detail below, the device 100 is sealed by one or more gaskets.

Figure 2A:
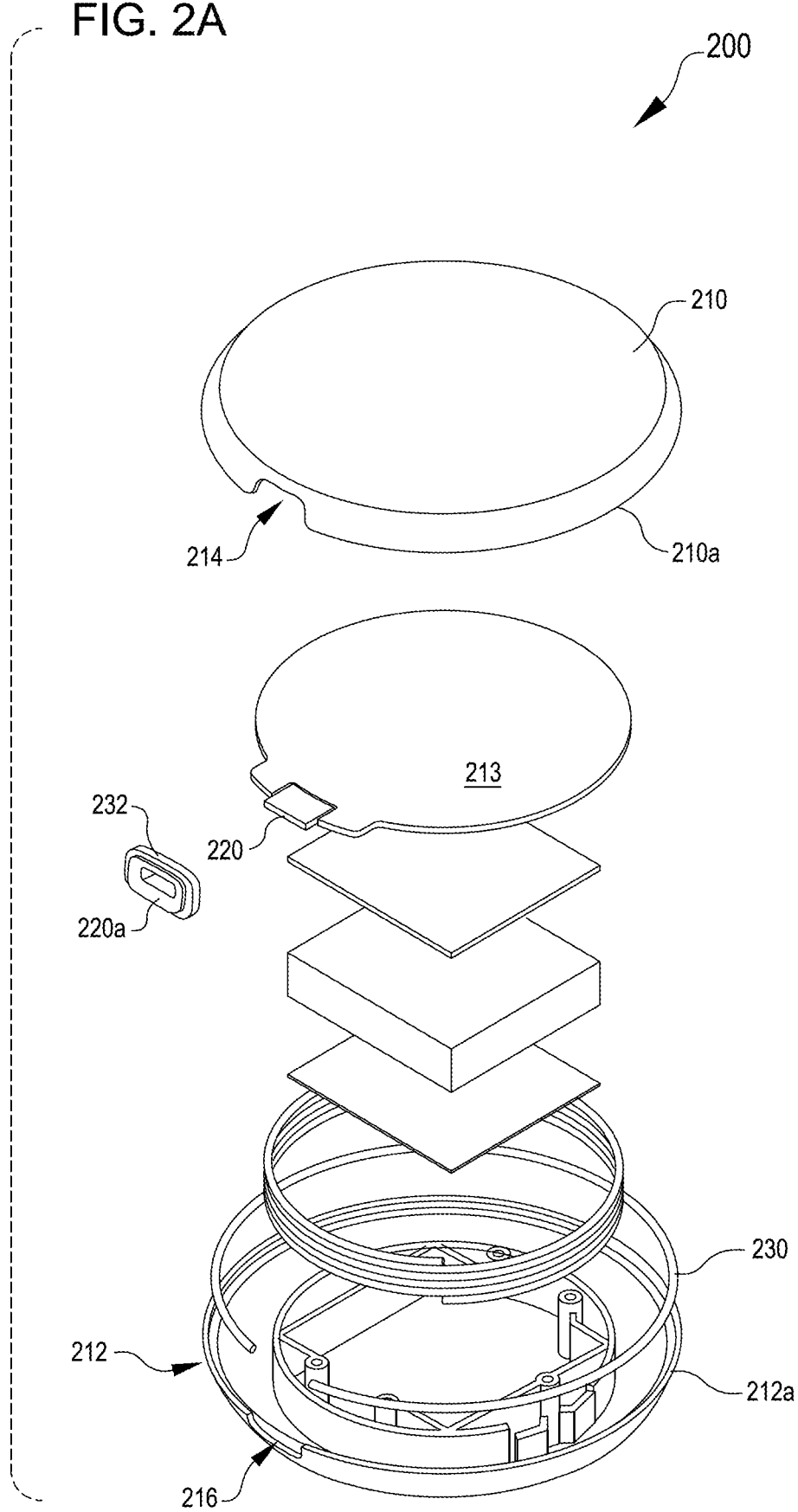
FIGS. 2A-2B show exploded views of an example wearable device having an electric charging port.
Figure 2B:
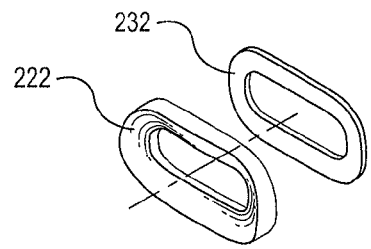

Referring now to FIGS. 2A-2B, FIG. 2A shows an exploded view of an example wearable device 200. The device 200 in this example is a wearable wireless charging and power-delivery device suitable for use with one or more implanted device, such as neurostimulators. The device 200 includes a PCB 213 with relevant electronics, such as a processor (e.g., a microcontroller), an RF transceiver, and an electrical connector 220. In this example, the electrical connector is a universal serial bus ("USB") C-type connector ("USB-C"), but may be any suitable electrical connector in various examples. For example, the electrical connector 220 may be any suitable USB-style connector, a power connector (e.g., connectable to a wall charger), a 3.5 mm headphone jack, etc. Further, while this example device 200 only includes one electrical connector 220, other example devices may include multiple electrical connectors.

In this example, the PCB 213 sits atop and is physically coupled, e.g., by a PSA, to a foam pad, which in turn is physically coupled to a housing portion 212. A coil antenna is positioned around the PCB 213 and is electrically connected to the RF transceiver when assembled.

As with the device 100 shown in FIGS. 1A-1B, this example device 200 includes two housing portions 210, 212 that together form a housing for the device. Further, and similar to the device 100 of FIGS. 1A-1B, this device 200 includes an electrical connector 220 that interrupts an interface between the two housing portions 210, 212 at an opening created by two partial openings 214, 216, one defined in each of the two housing portions 210, 212. The opening is partially formed in each of the housing portions 210, 212 by the respective partial openings 214, 216 formed in the respective housing portions 210, 212. The opening is then formed when the partial openings 214, 216 are aligned and the housing portions 210, 212 are joined together. It should be appreciated that the size and shape of the opening (and consequently the partial openings 214, 216) correspond to the type of electrical connector 220 employed in this example. Thus, in other examples, the opening may have a different size or shape. Further, in examples with multiple electrical connectors, there may be multiple openings formed in the device housing to accommodate each of the electrical connectors, though in some examples, multiple electrical connectors may share a single opening.

To seal the device 200 against moisture ingress, two gaskets 230, 232 are employed. Gasket 230 is formed from a foam material in a shape corresponding to the perimeter shape of the two housing portions 210, 212. The foam material has PSA applied to each side to adhere the gasket to a coupling surface 210a, 212a formed on each of the upper and lower housing portions. The gasket material may be supplied as a foam tape or may be cut from a foam pad or other suitable substrate. Further, while foam is employed as a gasket material in this example, any suitable gasket material may be employed, including compressible plastics.

In this example, the coupling surface 210a on one housing portion 210 protrudes from the housing portion 210, while the other coupling surface 212a is recessed within the other housing portion 212. The gasket 230 may then be placed against one of these coupling surfaces 210a, 212a and held in place by the PSA until it is pressed against the other coupling surface 210a, 212a when the two housing portions 210, 212 are joined and a then compressive force (the "sealing force") is applied to compress the gasket between the two housing portions 210, 212 to provide a seal.

As can be seen in FIG. 2A, gasket 230 has a gap in it corresponding to the opening formed in the housing to accommodate the electrical connector 220. Consequently, a second gasket 232 is employed to seal the electrical connector 220 against the housing. In this example, the electrical connector 220 has a portion that has been electrically coupled to the PCB, e.g., by soldering, and also includes a plate 220a that is physically coupled to the electrical connector 220, though in this exploded view, it is shown separately. The electrical connector plate 220a provides a substantially flat coupling surface to which gasket 232 may be affixed prior to assembly of the device 200. Once the gasket 232 is affixed to the electrical connector plate 220a, it may be pressed against the housing or another surface coupled to the housing to create a seal around the electrical connector 220 and the opening, while the electrical connector plate 220a is sealed against the electrical connector by a gasket integral to the electrical connector. In this example, a connector cover 222 is positioned within the opening and pressed against the gasket 232 to provide a seal. The gasket is thus pressed against interior surfaces of the housing, gasket 230 (as will be described in more detail below), and the connector cover 222 to seal the opening and to complete the seal of the device 200.

As mentioned above, gasket 232 interfaces with gasket 230 to provide a complete seal for the device 200. Because gasket 230 has a gap corresponding to the opening, though with some small overlap to provide surfaces to engage with gasket 232, it does not seal the opening. Further, the opening is perpendicular to the plane of the gasket 230 (or oblique to the plane at a different angle in some examples), complicating a seal of the entire device 200. To effect a complete seal, gasket 230 is pressed against and engages with gasket 232, as will be shown in more detail with respect to FIGS. 6A-6C.

In this example, gasket 232 is applied to the electrical connector plate 220a as discussed above and then the PCB 213 is positioned in the housing portion 212 on the foam pad assembly discussed above (it should be appreciated that the foam pad assembly is not required in some examples). The PCB 213 is then biased by an external force, e.g., a person's finger or a robotically controlled tool, to press the electrical connector plate 220a and gasket 232 against the housing to help establish the seal between the gasket 232 and the housing. In examples that employ a connector cover, it may be applied at this time or at a later time.

While the PCB 213 is biased as discussed above, it is securely coupled to the housing portion 212 using the screws depicted in FIG. 2A. It should be appreciated that any suitable coupling technique may be employed according to different examples to couple the PCB 213 to the housing portion 212 while the biasing force is maintained. By coupling the PCB 213 to the housing portion 212 while the PCB is biased, the biasing of the gasket against the housing (or other surface) may be maintained even after the initial external biasing force is removed. The maintained biasing force may then help maintain the seal between the gasket 232 and the opening. In addition, or instead of, the biasing force, additional material, such as a potting compound, may be applied around the perimeter of the opening or the electrical connector to further enhance the seal of the opening.

Once the PCB 213 (and other internal components) are installed within the housing portion(s) 210, 212, gasket 230 may be applied to one of the coupling surfaces 210*a*, 212*a* and the two housing portions may be pressed together and physically coupled using the screws depicted in FIG. 2A (or any other suitable coupling technique). The force applied by the screws may provide the sealing force to compress the gasket 230 and create a seal around the perimeter of the device 200. Further, compressing the gasket 230 also presses it against gasket 232, thereby completing the seal for the device 200. Thus, the device employs two gaskets oriented orthogonally to each other and engaged with each other to form a complete seal for the device against moisture or other contaminant ingress.

Figure 3:
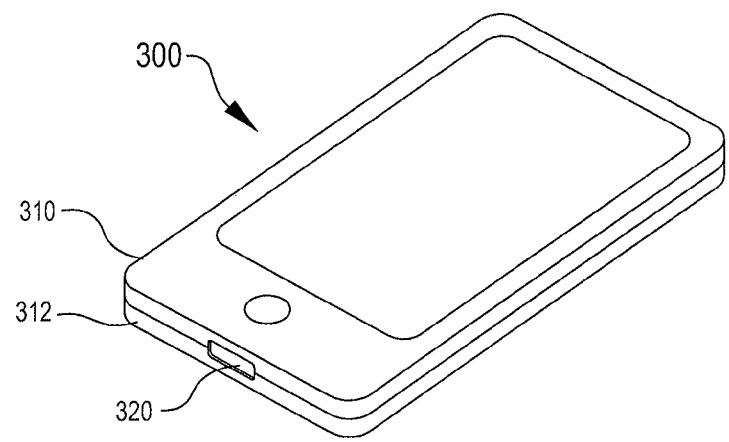
FIGS. 3-5 show example devices according to this disclosure.

It should be appreciated that the specific sizes and shapes of the components in FIGS. 2A-2B are examples of one device 200. Other examples according to this disclosure may have different housing shapes and profiles. For example, while a wearable wireless charging devices is shown in FIGS. 2A-2B, the device may be shaped or configured as a wristwatch, a continuous glucose monitor ("CGM") or other wearable biosensor, an insulin pump, a smartphone or tablet device, etc. Further, while the device 200 has a circular disc-shaped housing, other example devices may have other housing cross-sections, such as square, rectangular, triangular, etc., and may thus use gaskets corresponding to the shapes of such housings. For example, FIG. 3 shows an example smartphone 300 having a housing made from two housing portions 310, 320 having a rectangular shape while providing an opening to accommodate an electrical connector 320, similar to the device 200 shown in FIGS. 2A-2B.

Figure 4:
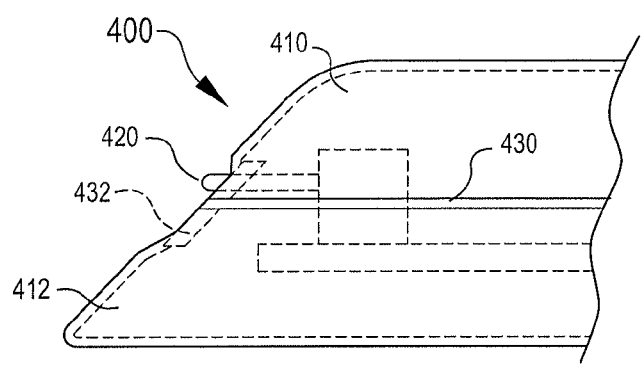
Figure 5:
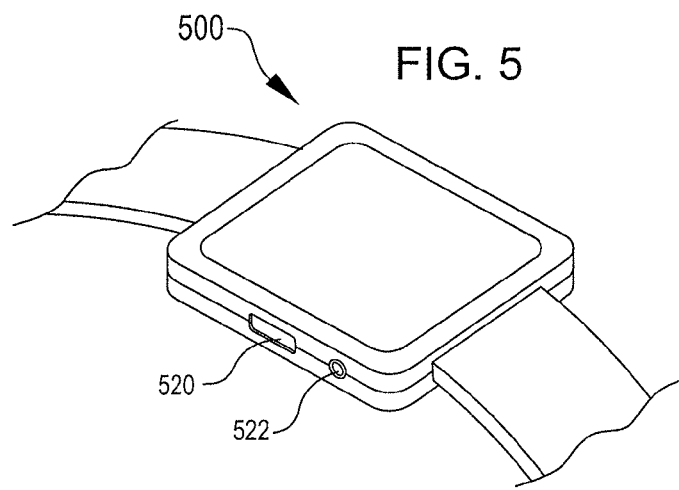

In addition, while the electrical connector 220 is positioned through an opening oriented substantially orthogonally to the gasket 230 sealing the housing portions 210, 212, orthogonality is not required. Instead, the opening may be defined at any angle oblique to the gasket 230 that may be appropriate for a particular implementation. For example, FIG. 4 shows a cross-section of a device 400 with a housing formed by two housing portions 410, 412 sealed by a gasket 430 that engages with another gasket 432 that seals an opening oriented at an oblique angle to gasket 430. Similar to the devices shown in FIGS. 2A-2B and 3, the opening provides access to an electrical connector 420. Further, some examples may have multiple openings, each of which may be sealed by a corresponding gasket that engages with a gasket sealing two housing portions of a device. For example, FIG. 5 illustrates a smartwatch device having two openings to support two different electrical connectors, such as an electrical charger and a 3.5 mm headphone jack. Still further configurations may be employed in other examples according to this disclosure.

Figure 6A:
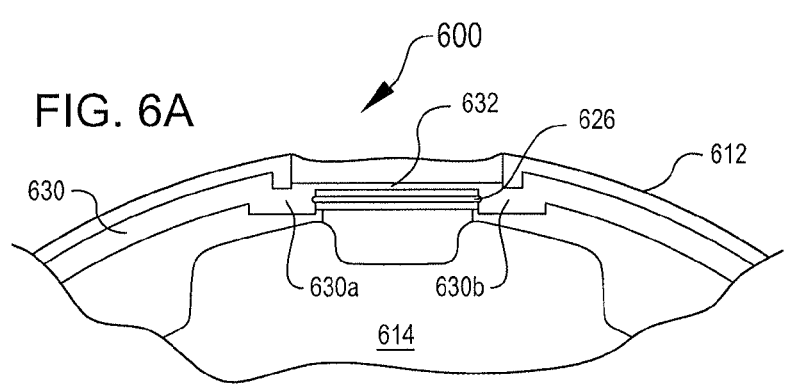
FIGS. 6A-6C show cut-away views of an example wearable device having an electric charging port.
Figure 6B:
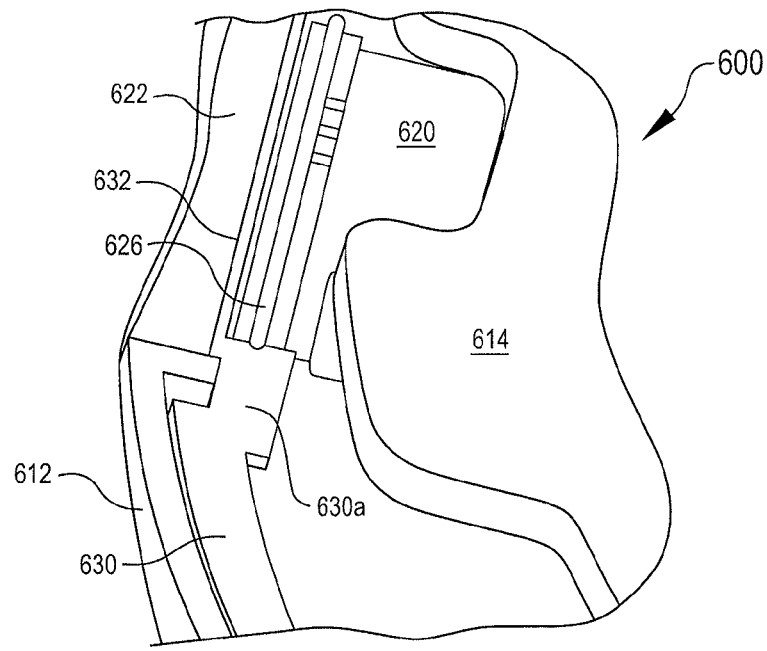
Figure 6C:
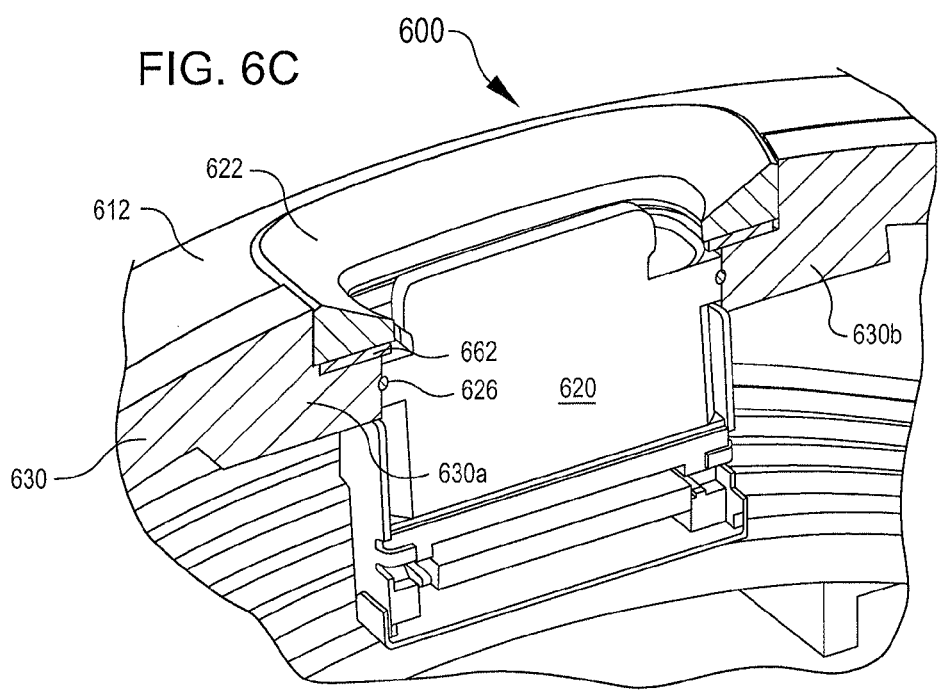

Referring now to FIGS. 6A-6C, FIGS. 6A-6C show cut-away views of an electronic device 600 having an opening to accommodate an electrical connector 620. FIG. 6A shows a cross-section of the device 600 and illustrates to engagement of a perimeter gasket 630 for the device and the electrical connector gasket 632. As is shown in FIG. 6A, as well as FIGS. 6B-6C, the electrical connector 620 is sealed against a connector cover 622 by gasket 632. The perimeter gasket 630 is shaped to correspond to a coupling surface defined by the housing portion 612 and includes a portion that deviates from the circular shape of the device 600 to instead correspond to the edge of the opening and to engage with gasket 632, labelled as tabs 630*a-b*. These tabs 630*a-b* are integrally formed as a part of the gasket, but are shaped as shown to enable engagement with gasket 632 and the opening in the housing.

In addition, the gasket tabs 630*a-b* are sized to engage with the electrical connector 620 itself. For example, the electrical connector 620 in this example has an O-ring 626 that runs around the perimeter of the electrical connector 620 to enable sealing of the electrical connector itself. The shape of the tabs 630*a-b* enable the gasket 630 to engage with the O-ring to provide a further seal. Thus, the device has a first seal created by gasket 630 between the housing portions of the device, a second seal created by gasket 632 around the opening, a third seal between gasket 630 and 632, and a fourth seal between gasket 630 and the O-ring 626. The creation of these multiple seals may help to further seal the device against moisture (or other contaminant) ingress.

Figure 7A:
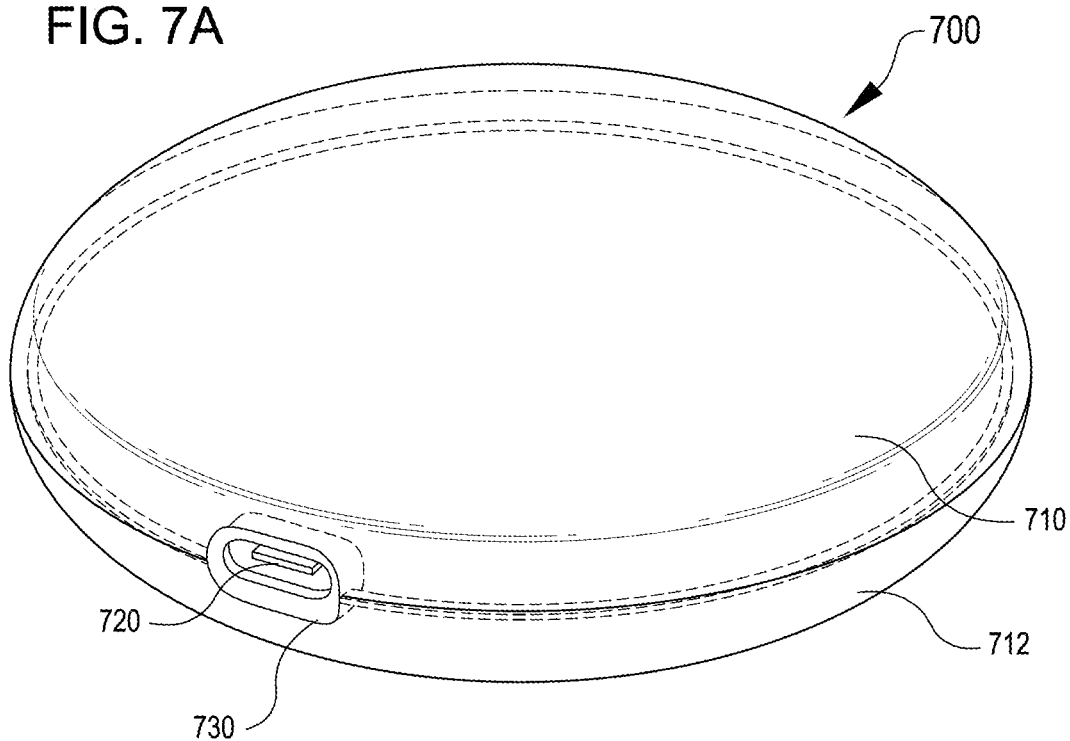
FIGS. 7A-7B show an example wearable device and sealing component.
Figure 7B:
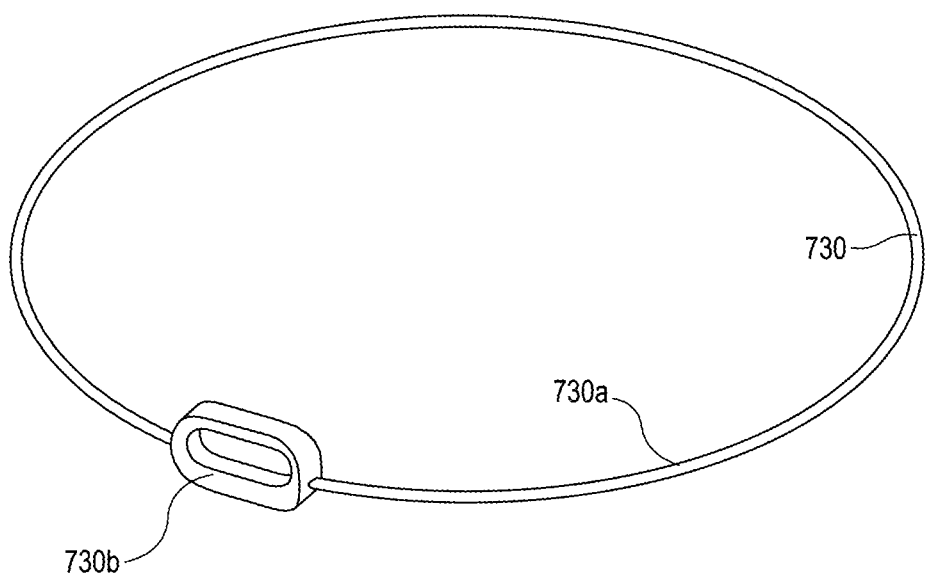

FIGS. 7A-7B show another example device 700 according to this disclosure. In this example, however, rather than using two different gaskets, the device is sealed by a single gasket 730. Similar to some other example devices according to this disclosure, the device 700 has a housing formed from two housing portions 710, 720 that are coupled together. In addition, the housing forms an opening to enable access to an electrical connector 720.

As described above, a gasket 730 is positioned between the two housing portions 710, 712 to engage with sealing surfaces formed on each housing portion 710, 712. When the housing portions 710, 712 are coupled together, they compress the gasket 730, forming a seal between the housing portions 710, 712. However, as shown in FIG. 7B, the gasket 730 is formed to have both a perimeter portion 730*a* and an opening portion 730*b*. The perimeter portion 730*a* seals the housing portions 710, 712 to each other, while the opening portion 730*b* seals the housing portions 710, 712 to the electrical connector 730 and seals the electrical connector 730 within the opening. Thus, gasket 730 integrates two gaskets, such as gaskets 230 and 232, into a single gasket to seal the entire device. As with the gaskets discussed above, gasket 730 may be constructed from any suitable material, such as a foam material with a PSA applied to each side to assist with aligning the gasket 730 with the housing portions and sealing the device 700.

The gasket shown in FIGS. 7A-7B may simplify the manufacturing process of some example devices since only a single gasket is needed. Thus, alignment and engagement of two different gaskets to each other is avoided. However, manufacturing of the gasket 730 itself may be more complex.

Referring now to FIGS. 8A-8C, FIG. 8A shows an example gasket 830 usable for sealing wearable electronic devices according to this disclosure. In this example, similar to the example shown in FIG. 7B, the gasket 830 is constructed of a single piece of material suitable to seal both a housing portions to each other as well as sealing an electrical connector, e.g., electrical connector 720, to the housing. The gasket 830 has a perimeter portion 830*a* and an opening portion 830*b*. As with the example gaskets illustrated in the figures and as discussed above, the gasket 830 is shaped to correspond to the perimeter shape of a wearable device. In this example, perimeter portion 830*a* is shaped to correspond to the perimeter of the device 700 shown in FIG. 7A. The opening portion 730*b* is shaped to correspond to the shape of the opening and to mate with the electrical connector 720 and the housing.

In this example, the gasket is formed from a single piece of material, e.g., via laser cutting, stamping, etc., and is configured to be folded to create the opening portion 830*b*. The fold is illustrated in FIG. 8C with the opening portion folded to be in a plane orthogonal to the plan of the perimeter portion 830*a*. As discussed above, however, the relationship between the two gasket portions need not be orthogonal, but instead may have an oblique alignment, such as shown in FIG. 4. Further, in this example, the gasket material has a PSA applied to each side of the material, enabling the folded portions of the opening portion 830 to seal to each other as well as adhere to and remain in place on the housing portions or against the electrical connector during assembly of the device 700. In some example, however, a PSA may be applied to the housing portions instead, or in addition to, the gasket itself. Such a technique is equally applicable to each of the example gaskets discussed herein.

Example gaskets according to the gasket 830 shown in FIGS. 8A-8C may be advantageous as they may be relatively simply to form by cutting the gasket from a single sheet of material, rather than using a molding process, which may be needed for the example shown in FIG. 7B.

As discussed above, while the example device 700 and gaskets 730, 830 shown in FIGS. 7A-7B and 8A-8C have a particular shape and size, each may have any suitable size and shape, such as the sizes and shapes discussed above with respect to FIGS. 3-5. Further, while the gaskets 730, 830 shown in FIGS. 7A-7B and 8A-8C each have only one opening portion 730*b*, some examples may include multiple opening portions to accommodate multiple openings defined in a device housing, such as shown in FIG. 5.

Referring now to FIG. 9, FIG. 9 shows an example method 900 of sealing wearable electronic devices. The example method 900 will be discussed with respect to the example device 200 shown in FIGS. 2A-2B; however, example methods according to this disclosure may be employed with respect to any suitable devices according to this disclosure.

At block 910, first and second housing portions 210, 212 are obtained and provided for the assembly process. In this example, the housing portions 210, 212 have circular shapes and together form a housing having a circular disc shape. However, it should be appreciated that any suitable housing shape may be employed, such as discussed above with respect to FIGS. 3-5. Further, the device housing may be composed of multiple different components. For example, as can be seen in FIG. 2A, the housing has a generally rectangular plate that is affixed to a cavity formed in housing portion 210. Such a plate may cover other openings in the housing, such as for a speaker or one or more light emitters, such as one or more light emitting diodes ("LEDs"). However, the housing portions 210, 212 form the portion of the housing that protects the electronics positioned on the PCB 213 in this example and are the housing portions 210, 212 that are sealed by a perimeter gasket 230 and an opening gasket 232, even if other gasket seals are used, such as to seal an opening for a speaker or one or more LEDs.

At block 920, a gasket 230 is coupled to one of the first or second housing portions. As discussed above with respect to FIG. 2A, each housing portion 210, 212 defines a coupling surface 210*a*, 212*a*. These coupling surface will interface and engage with each other when the housing portions 210, 212 are coupled to each other. Thus, in this example, the gasket 230 is coupled, e.g., using a PSA applied to the gasket material or to one of the coupling surfaces, to one of the coupling surfaces 210*a*, 212*a*. In some examples the gasket 230 may simply be laid in position on one of the coupling surfaces without the use of any adhesive or similar coupling mechanism. For example, coupling surface 212*a* is recessed below the outer perimeter of the housing portion 212 and thus, the gasket 230 may simply be laid on the recessed coupling surface 212*a*, where it may stay in place within the recess. Still other approaches to positioning or coupling the gasket 230 to one of the housing portions 210, 212 may be employed.

At block 930, a second gasket 232 is coupled to an electrical connector plate 220*a* of the electrical connector 220, which is electrically coupled to a PCB 213 and is to be positioned within the housing. As shown in FIG. 2A, the electrical connector 220 has a connector plate 220*a* coupled to it, and the gasket 232 is coupled to the connector plate 220*a* by way of a PSA applied to the gasket material. However, a PSA is not required. In some examples, the gasket may be pressed into place over an flange on the connector plate, which holds the gasket in place until the device 200 is fully assembled.

At block 940, the PCB 213 is positioned within one of the housing portions 210, 212 and a biasing force is applied to the PCB 213 to press it towards the partial opening 214, 216, which may enable the gasket 232 to engage with the housing portion 210, 212 or to otherwise position the electrical connector plate 220*a* and gasket 232 in place to create a seal for the opening. In this example, the PCB 213 is coupled to a foam pad by a PSA, and the foam pad is in turn coupled to the housing portion 212 by another PSA. Once this assembly is in place within the housing portion 212, the biasing force is applied. It should be appreciated that a biasing force is not required in every example according to this disclosure. Instead, it may be employed in some examples to help provide a robust seal for the opening. However, in some examples, the position of the PCB and electrical connector plate 220*a* may be sufficient to seal the opening without an additional biasing force. For example, as discussed above with respect to FIGS. 6A-6C, the electrical connector 620 may include an O-ring 626 that encircles the outer perimeter of a portion of the electrical connector 620. This O-ring 626 may engage with the perimeter gasket 620, which may help seal the device. In such an example, a biasing force may not be needed as the opening gasket may seal the opening by engaging with the housing, while the O-ring may further supplement the seal provided by the opening gasket by engaging with the perimeter gasket 620. In addition, in some examples, an additional sealing material, such as a potting compound may be applied around the perimeter of the electrical connector to further seal the opening against moisture ingress.

At block 950, the PCB 213 is physically coupled to the housing to hold it in place and, if a biasing force was applied, to maintain the biasing force. In an example where a biasing force is applied, this may deflect the foam pad the PCB 213 is resting on. If the PCB 213 is not coupled by an additional mechanism, the PCB 213 may return to an unbiased position when the biasing force is removed. Thus, in this example, screws are used to physically secure the PCB 213 to the housing portion 212. The screws can then maintain the biasing force on the PCB 213 and maintain the seal at the opening. If no biasing force is needed, a PSA may be sufficient to couple the PCB 213 to the housing portion; however, screws or rivets or other coupling mechanisms may be employed as well.

At block 960, the two housing portions 210, 212 are pressed together to apply a sealing force to the gasket 230 and are coupled together, such as by using screw, rivets, etc.

At block 970, the opening gasket 232 engages with the other housing portion 210, 212, e.g., the housing portion other than the one the PCB 213 is coupled to, and also engages with the perimeter gasket 230, if it was not already engaged, e.g., the PCB 213 was affixed to one housing portion 210, while the perimeter gasket 230 was initially coupled to the other housing portion 212. Further, if an additional component is used to seal the opening, e.g., a connector cover 222, it is pressed into place within the opening to complete the seal of the opening. After performing the couplings and engagements discussed with respect to block 970, the seal between the two housing portions 210, 212 is complete as is the seal of the electrical connector at the opening.

It should be appreciated that the ordering of the blocks in the example method 900 above are not required and other orders may be employed. For example, blocks 920-950 may be performed in a different order, such as by first positioning the PCB 213 within the housing portion 212 and then applying the gasket 232 to the electrical connector 220, and then applying the perimeter gasket to one of the housing portions 210, 212.

Further, it should be appreciated that this example method 900 may not be sufficient to entirely assemble the device 200. Still other steps may be employed, such as to affix a cover plate, e.g., with a logo or product name, to the housing or to insert other components within the housing before it is sealed.

Referring now to FIG. 10, FIG. 10 shows another example method 1000 of sealing wearable electronic devices. The example method 900 will be discussed with respect to the example device 700 shown in FIGS. 7A-7B; however, example methods according to this disclosure may be employed with respect to any suitable devices according to this disclosure.

At block 1010, first and second housing portions 710, 712 are obtained and provided for the assembly process generally as discussed above with respect to block 910.

At block 1020, the gasket 730 is coupled to one of the first or second housing portions generally as discussed above with respect to block 920. In this case, however, because the gasket 730 includes an opening portion 730*b*, the opening portion of the gasket 730*b* is positioned within the partial opening of the respective housing portion 710, 712.

At block 1030, an electrical connector 720 electrically coupled to a PCB an electrical connector cover, affixed to the electrical connector, is inserted within the opening portion 730*b* of the gasket 730, which engages with the electrical connector 720, e.g., with the electrical connector plate portion of the electrical connector, generally as discussed above. It should be appreciated that block 1030 may be performed before block 1020 to engage the electrical connector 720 with the gasket 730 before the gasket 730 is positioned on one of the housing portions 710, 712.

At block 1040, a PCB is positioned within one of the housing portions 710, 712 and a biasing force is applied to the PCB generally as discussed above with respect to block 940. However, similarly to the example discussed above with respect to FIG. 9, the biasing force need not be employed in some examples.

At block 1050, the PCB is physically coupled to one of the housing portions 710, 712 generally as discussed above with respect to block 950.

At block 1060, the two housing portions 710, 712 are pressed together to apply a sealing force to the gasket 730 and are coupled together, generally as discussed above with respect to block 970.

Figure 11A:
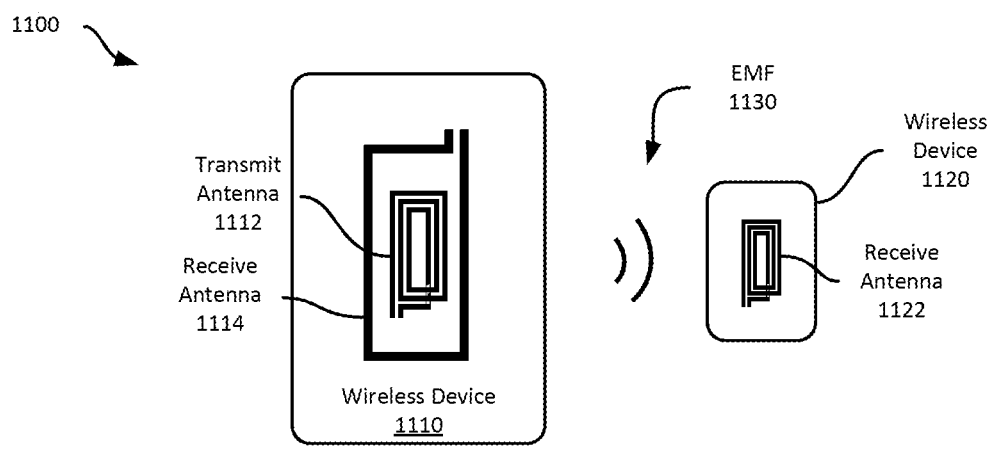
FIG. 11A shows an example system for dynamic control of near-field wireless power.
Figure 11B:
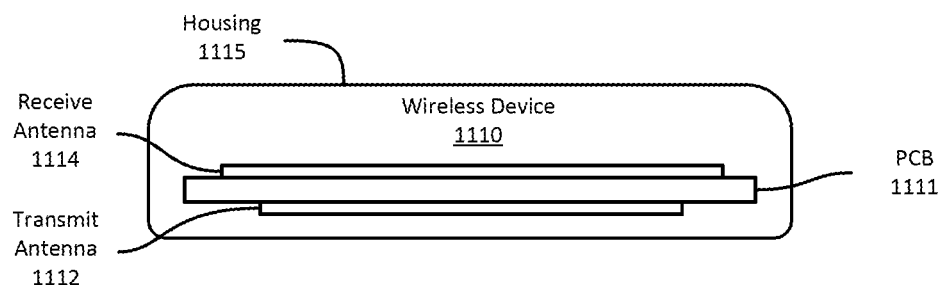
FIG. 11B shows a cross-sectional view of an example wireless device for dynamic control of near-field wireless power.

Referring now to FIGS. 11A-11B, FIG. 11A illustrates an example system for dynamic control of near-field wireless power. The system 1100 in FIG. 11 includes two wireless devices 1110, 1120. Wireless device 1110 will be referred to as charger device 1110, though this does not imply that the charger device 1110 (or any other "charger device" according to this disclosure) is only suitable for use as a battery charger. Rather, the charger device 1110 is capable of generating an EMF that may be used to provide electrical energy to another wireless device 1120, which will be referred to as the target device 1120.

As can be seen in FIG. 11A, the charger device 1110 includes a transmit antenna coil 1112. The charger device 1110 transmits current through the transmit antenna coil 1112 to generate an EMF 1130. To supply power to the target device 1120, the charger 1110 device is brought into proximity to the target device 1120 and generates the EMF 1130, which while depicted as being a signal transmitted to the target device 1120, is actually a field surrounding the charger device 1110. The target device 1120 is positioned within the field. The target device's receive antenna coil 1122 then couples with the EMF 1130 to obtain electrical energy. In addition, the charger device 1110 employs a second antenna coil—receive antenna coil 1114—to also obtain energy from the EMF 1130.

In this example, receive antenna coil 1114 is positioned concentrically to the transmit antenna coil 1112. Such an arrangement may provide a more efficient coupling between the receive antenna coil 1114 and the EMF 1130; however, it should be appreciated that the transmit and receive antenna coils 1112, 1114 need not be arranged concentrically around a common axis.

Referring to FIG. 11B, FIG. 11B illustrates a cross-section of the charger device 1110 to show the arrangement of the transmit and receive antenna coils 1112, 1114. In this example, while the two antenna coils 1112, 1114 are arranged concentrically, they are not co-planar. Specifically, in this example, the transmit antenna coil 1112 is positioned on one side a printed circuit board ("PCB"), while the receive antenna coil 1114 is positioned on the other side of the PCB, all of which are positioned within the wireless device's housing 1115. Such an arrangement may be used due to positioning of other electronic components on the PCB. However, it should be appreciated that in some examples, the two antenna coils 1112, 1114 may be co-planar. Further, whether the two antenna coils 1112, 1114, are arranged concentrically or not is independent of whether they are co-planar with respect to each other.

Figure 12:
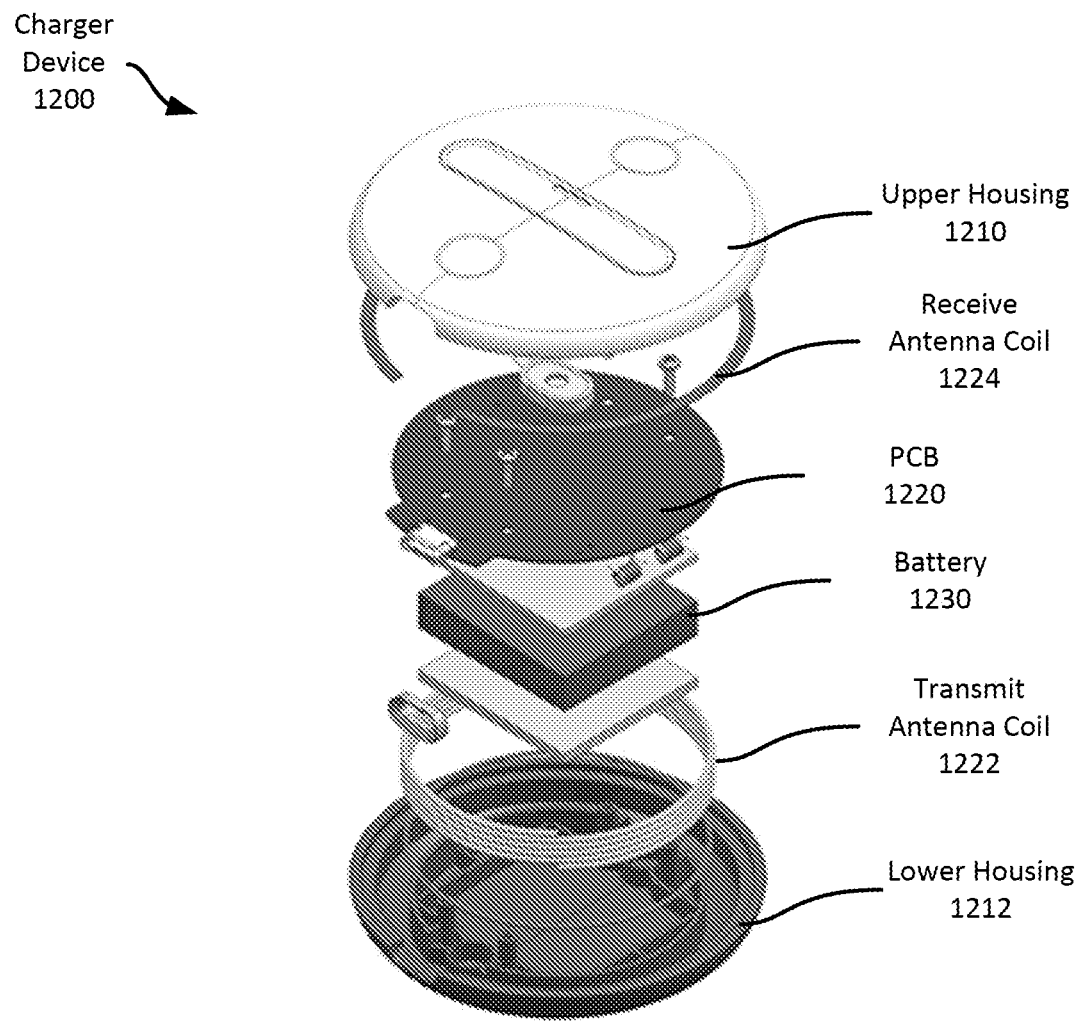
FIG. 12 shows an exploded view of an example device for dynamic control of near-field wireless power.

Referring now to FIG. 12, FIG. 12 shows an exploded view of an example charger device 1200 for dynamic control of near-field wireless power. The example charger device 1200 shown in FIG. 12 includes two housing portions, upper housing 1210 and lower housing 1212. Positioned within the housing are a PCB 1220, to which are coupled a transmit antenna coil 1222 and a receive antenna coil 1224 that has been formed as a trace on the PCB 1220. As can be seen, the transmit and receive antenna coils 1222, 1224 are concentrically aligned, but are not co-planar. The PCB 1220 also has several electronic components coupled to it, including a processor, a wireless field driver, and an EMF sensor. A battery 1230 is included to provide power for the electronic components as well as to supply current to generate an EMF to transmit power to a target device.

Figure 13:
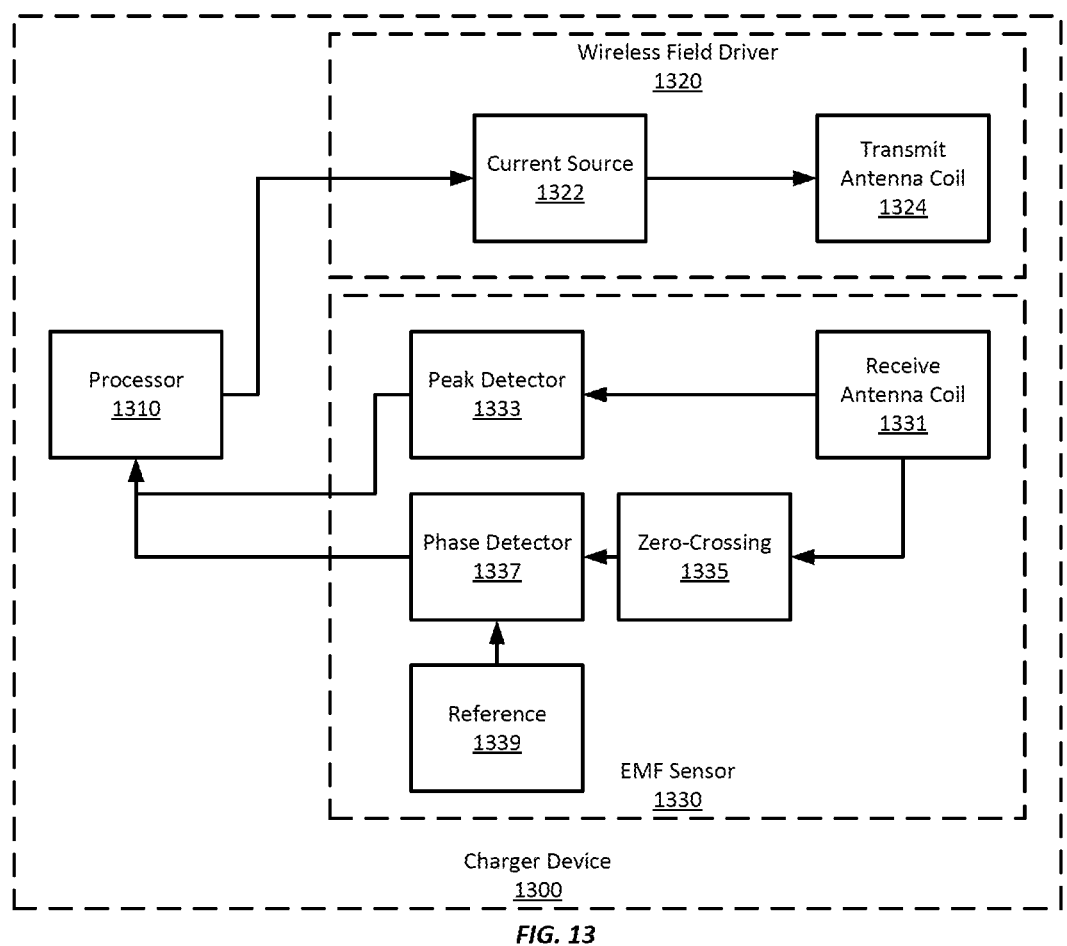
FIG. 13 shows an example device for dynamic control of near-field wireless power.

Referring now to FIG. 13, FIG. 13 illustrates an example wireless device 1300 for dynamic control of near-field wireless power. In this example, the charger device 1300 includes a wireless field driver 1320 and an EMF sensor 1330, both of which are connected to processor 1310. The wireless field driver 1320 is configured to generate an EMF in response to a command from the processor 1310. To do so, the wireless field driver 1320 includes a current source 1322 and a transmit antenna coil 1324.

In this example, the current source 1322 is a switching power amplifier, such as a high-efficiency switching amplifier. One example of such a switching power supply is discussed below with respect to FIGS. 15-17. An advantage of using of such a power supply may include real-time adjustment of the power amplifier to reduce power consumption while maintaining a target EMF strength. However, it should be appreciated that any suitable variable alternating current ("AC") power source may be employed to generate and transmit an alternating current to the transmit antenna coil 1324. In response to such a current, the transmit antenna coil 1324 generates an alternating EMF that can be used to provide electrical power to a target device, e.g., target device 1120 shown in FIG. 11A.

The EMF sensor 1330 in this example includes a receive antenna coil 1331 that couples with the EMF generated by the wireless field driver 1320 and outputs an AC signal based on the strength of the field. The receive antenna coil 1331 is electrically coupled to a peak detector 1333 and a zero-crossing detector 1335. The output of the peak detector 1333 is electrically coupled to the processor 1310 to provide signals to the processor 1310 indicating the magnitude of the EMF. The zero-crossing detector 1335 is coupled to a phase detector 1337, which receives the output from the zero-crossing detector 1335 and a reference signal 1339 to detect a phase change in the EMF. The output of the phase detector is electrically coupled to the processor 1310 to transmit signals indicating phase information about the EMF.

With respect to the peak detector 1333, any suitable peak detector may be employed. For example, a simple peak detector may be implemented by a diode in series with a capacitor coupled to the receive antenna coil 1214. The voltage across the capacitor will then indicate the magnitude of the AC signal. However, more complex peak detectors may be employed depending on the application.

With respect to the zero-crossing detector 1335, any suitable zero-crossing detector, such as commercially available semiconductor zero-crossing detector devices. Alternatively, a suitable electrical circuit may be used, such as a comparator coupled to the receive antenna coil 1214. The output of the zero-crossing detector 1335 is provided to the phase detector 1337, which also receives a reference signal 1339, e.g., based on the AC signal output by the current source. The phase detector 1337 then detects a phase difference between the output signal from the zero-crossing detector and the reference signal. The output of the phase detector 1337 in this example is a voltage indicating the difference in phase between the zero-crossing detector signal and the reference signal, and is provided to the processor 1310 to indicate the phase change of the generated EMF.

The processor 1310 in this example is a microcontroller that executes processor-executable instructions stored in a memory (not shown) to receive the peak detector signals to estimate the strength of the EMF; however, it should be appreciated that any suitable processor may be employed, including application-specific integrated circuits ("ASIC"). The processor 1310 also uses the phase detector signals to estimate the load impedance of the target device, to detect foreign objects located between the charger device 1300 and target device, or such objects in close proximity to the charger device 1300. It may also determine potential harmful EMI effects and reduce the strength of the EMF accordingly.

In response to receiving the peak detector signal, the processor 1310 estimates the strength of the EMF and determines a difference between it and the target strength of the EMF. If the estimated strength is different than the target strength, the processor 1310 either increases or decreases the amount of current output by the current source 1322 to adjust the strength of the EMF. By iteratively adjusting the current source's output current, the processor 1310 is able to adjust the strength of the EMF until it matches or is within a threshold amount of the target EMF strength. Example techniques for iteratively adjusting the output current are discussed below with respect to FIG. 14.

In response to receiving the phase signal from the phase detector, the processor 1310 can estimate a load impedance presented by the target wireless device. The estimated load impedance may be employed to tune adjust a duty cycle of the current source 1322 to better match the load impedance. Alternatively, or in addition, a target device may adjust its load impedance, e.g., by activating and deactivating electronic functionality, to communicate information to the charger device 1300. For example, the target device may adjust its presented impedance to output data at a fixed bit rate, e.g., 1 bit per millisecond, which may be detected by changes in phase shifts detected by the phase detector. Such a data transmission technique may be used to provide information about the status of the target device, e.g., estimated received EMF strength, estimated power received, estimated power requirements, battery charge level, etc. Such information may then be employed to adjust the strength of the EMF.

For example, the processor 1310 may determine a difference between the estimated EMF strength determined by the charger device 1300 and the estimated EMF strength received from the target device. The difference may indicate a distance between the charger device and the target device and may be used to scale the target EMF strength based on the decrease in signal strength over distance according to an inverse-square relationship. In some examples, estimated power requirements received from the target device may be used to adjust a target EMF strength based on a difference between the estimated EMF strength determined by the charger device (or the target device) and the estimated power requirements.

Figure 14:
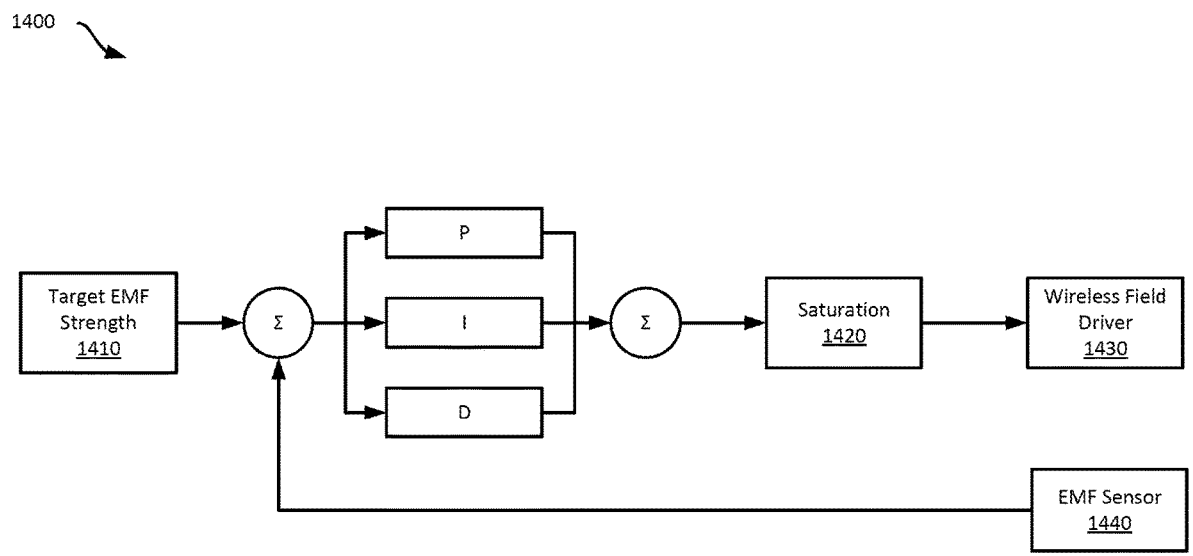
FIG. 14 shows an example technique for dynamic control of near-field wireless power.

Referring now to FIG. 14, FIG. 14 shows an example technique for dynamic control of near-field wireless power that may be employed by a processor of a charger device, e.g., the processor 1310 shown in FIG. 13. In this example, the technique employs a PID control system 1400 to adjust an output current of a wireless field driver 1430. The control system 1400 accepts a target EMF strength 1410 as an input signal and the output of an EMF sensor 1440, e.g., the output of the peak detector 1333 of FIG. 13, as an error signal. The input and error signals are summed to obtain the error, which is provided to each of the P, I, and D portions of the PID controller. The outputs of these three blocks are summed to provide an adjusted control signal to the wireless field driver to adjust the amount of current output to the transmit antenna coil. The summation of these three terms may be represented by the following equation:

$$i_{tx}(t) = K_p e(t) + K_i \int_0^i e(t')dt' + K_d \frac{de(t)}{dt}$$

Where the $K_p$, $K_i$, and $K_d$ terms represent coefficients for the P, I, and D terms, respectively, and the function e(t) represents the error signal over time. Adjusting the coefficients changes the response of the control system to the detected error, depending on the desired convergence time, allowable overshoot, etc. For example, a suitable transfer function may be designed based on desired pole and zero positions.

The technique 1400 shown in FIG. 14 also includes a saturation function 1420 that applies saturation limits to the output from the PID controller to limit the maximum output current or to limit the rate of change of the output current. For example, the saturation function 1420 may output a fixed saturation value if the output of the PID controller exceeds a threshold, e.g., if the PID controller outputs a signal indicating a current of 300 milliamps, while the current source is only capable of outputting a maximum of 100 milliamps, the saturation function 1420 may output a signal to cause the current source to output a current of 95 milliamps (or another value).

The PID controller shown in FIG. 14 operates iteratively over time to change the current output by the wireless field driver, thereby adjusting the strength of the EMF generated by a transmit antenna coil. Over successive iterations, the PID controller causes the estimated strength of the generated EMF to converge on the target EMF strength, provided the wireless field driver is capable of outputting a sufficiently strong EMF.

It should be appreciated that while this example employs a PID controller, one or two of the P, I, or D terms may be eliminated to provide a desired control system, e.g., a PI or a PD control system. Such alternative control system approaches may be suitable in different implementations, depending on system complexity or design requirements.

Figure 15:
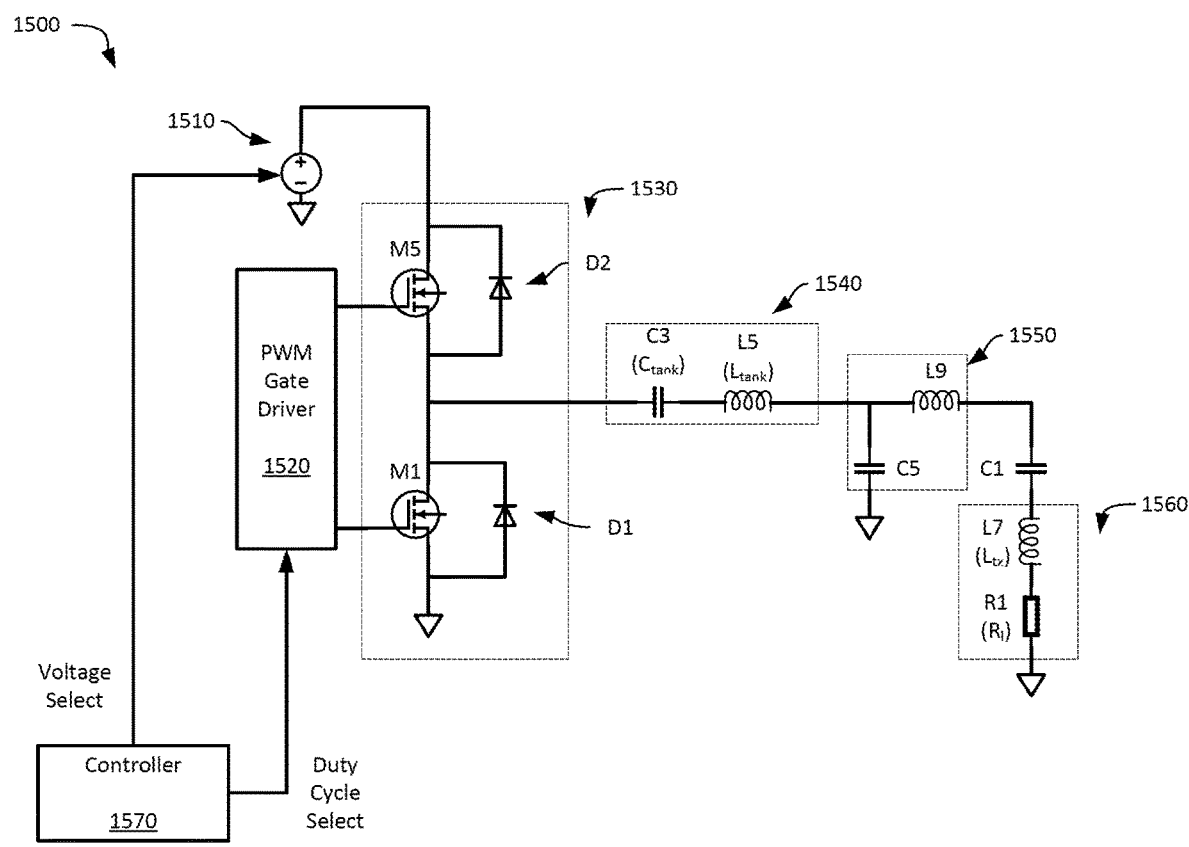
FIG. 15 shows an example adjustable power amplifier suitable for use with example systems for dynamic control of near-field wireless power.

Referring now to FIG. 15, FIG. 15 shows an example adjustable power amplifier suitable for use with example systems for dynamic control of near-field wireless power. The example system 1500 includes a DC/DC power supply 1510 with selectable output voltage, as discussed above with respect to FIG. 1. It should be appreciated that any suitable DC power supply with an adjustable DC output voltage may be employed as the power supply 1510, including adjustable AC/DC supplies. The power amplifier includes two MOSFETs M1-M2 arranged as switches in a half-bridge configuration. The PWM gate driver 1520 is connected to the gates of each of the MOSFETs M1-M2 and toggles the gates to switch them on and off. The PWM gate driver 1520 maintains the MOSFETs M1-M2 in opposite states, such that M1 has the opposite state—on or off—as M2, and operates them in a ZVS and ZCS mode. The PWM gate driver 1520 toggles the switches according to a duty cycle selected by a controller (not shown) to provide an output signal to the tank circuit 1540, which in combination with the low pass filter 1550, provides the impedance transformation network. The output of the low-pass filter 1550 is provided to the load 1560, which includes the transmit coil L7 and the receive coil and circuitry, represented by resistance $R_1$ (R1). The controller 1570 provides a duty cycle select signal to the PWM gate driver 1520 and provides a voltage select signal to the DC/DC converter 1510.

In this example, each MOSFET M1-M2 has a respective diode D1-D2 coupled between its source and drain to circulate power through the respective MOSFET M1-M2, thereby allowing the power amplifier to accommodate a larger amount of load reactance. Schottky diodes, having low voltage drops, may be employed as D1-D2 to provide efficient circulation of energy, though other types of diodes may be employed according to some examples. Further, while the MOSFETs M1-M2 are operated substantially in a ZVS and ZCS mode, variations in load reactance may result in ZVS and ZCS conditions not being met across the entire range of load reactances, though such a configuration may still enable reduced power dissipation across the entire range of load reactances.

The tank circuit 1540 is configured to operate in resonance at the desired transmission frequency, such as by providing substantially 0 ohms of resistance at resonance, or it may be employed to provide a predetermined impedance shift away from a resonant frequency. The filter 1550 is used to both provide low pass filtering of the power amplifier output, as well as to convert a range of load impedances to a predetermined range of impedances to present to the power amplifier 1530. The range of load impedances may then be used by the controller 1570 to select duty cycles for the PWM gate driver 1520.

Figure 16:
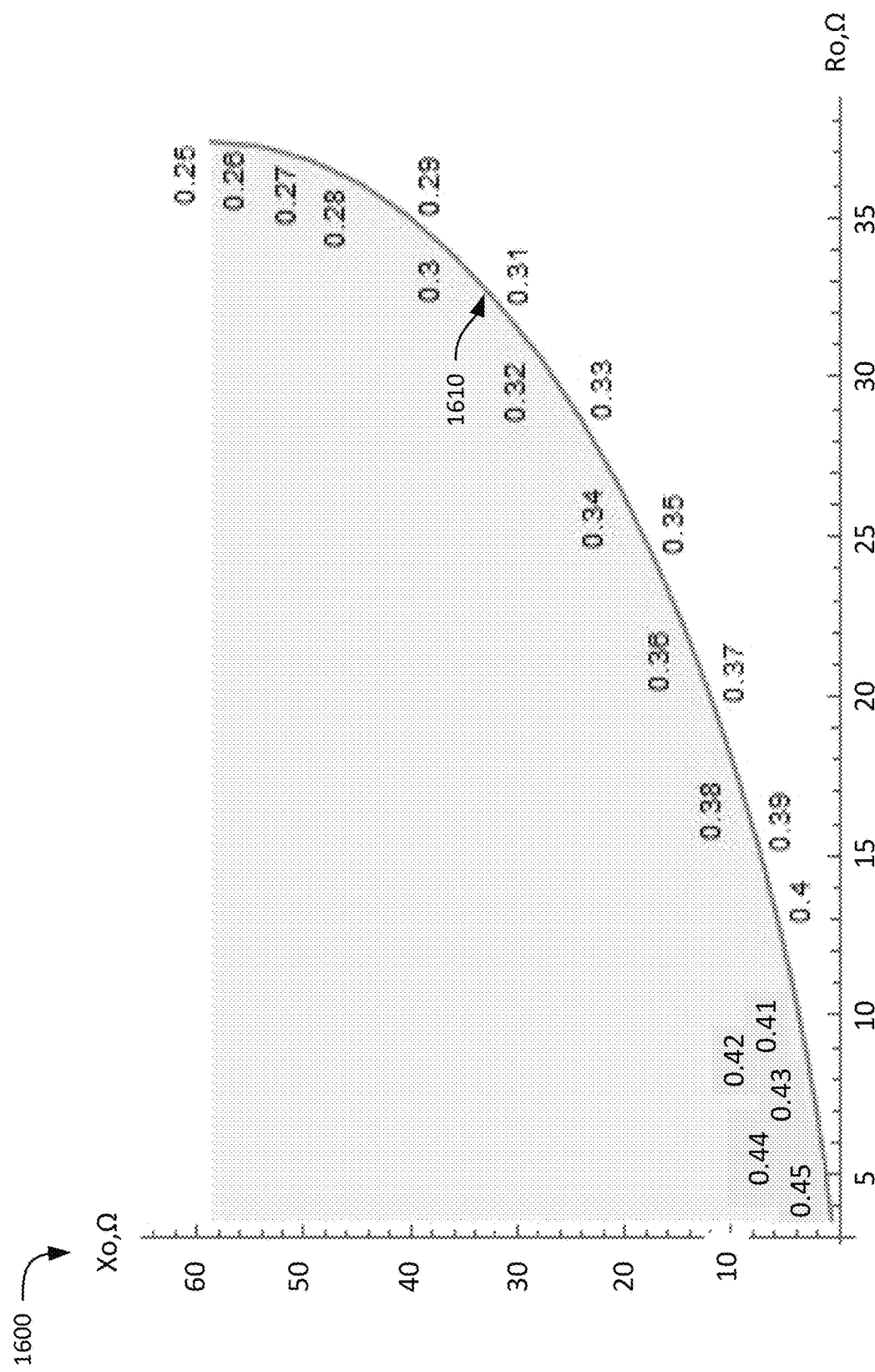
FIGS. 16-17 show example plots of duty cycles to achieve high efficiency for a power amplifier at a target impedance.

For example, referring to FIG. 16, FIG. 16 shows a plot 1600 of duty cycles to achieve high efficiency at a target impedance within an impedance plane, where the x-axis represents resistance and the y-axis represents reactance. As can be seen, a curve 1610 represents a correspondence between a duty cycle (normalized to a range from 0 to 1) and a load impedance. The points on the curve 1610 represent the duty cycle for a particular impedance that provides optimal efficiency of power transfer from the power amplifier at that impedance. Deviation from the curve 1610, such as due to limitations of the tank circuit and filter 1550, may result in reduced efficiency in power transfer, however, as will be seen with respect to FIG. 17, close approximations to the curve 1610 may still provide relatively efficient power transfer. The design of a circuit may affect the range of impedances within which the power supply 1510 can efficiently transfer power to a target device. For example, the relatively simple impedance transformation network, including filter 1550 shown in FIG. 15, may closely approximate the curve 1610 over a small range of impedances before substantially deviating. More complex impedance transformation networks may be designed to allow a power supply to approximate the curve 1610 over a wider range of load impedances, though such impedance transformation networks may require more physical layout space.

Figure 17:
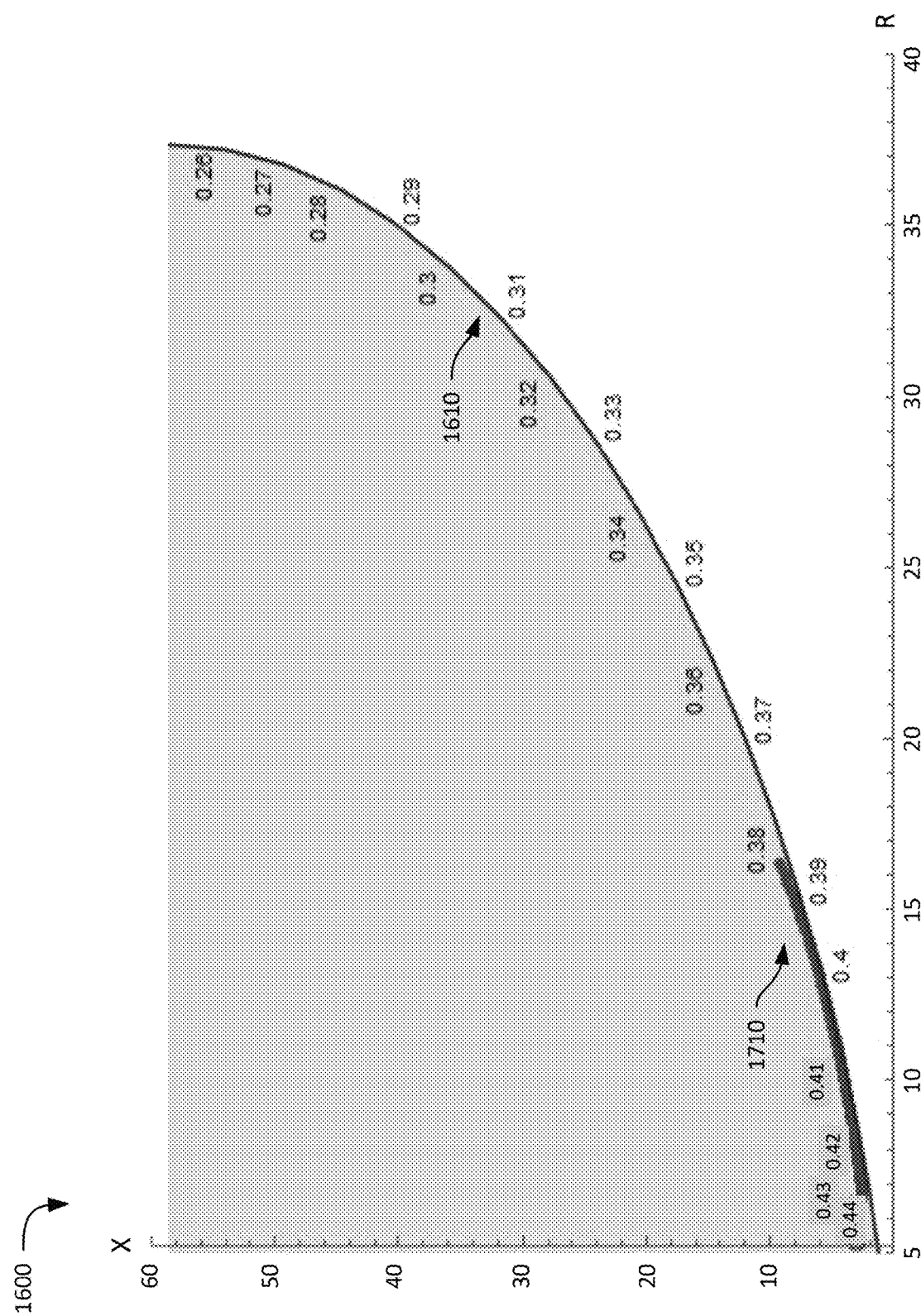

The filter 1550 in this example employs a capacitor C5 and an inductor L9 and provides an approximation of the curve 1610 shown in FIG. 16 over a range of load inductances as shown in FIG. 17. In this example, C3 has a value of 26.3 nanofarads ("nF") and the inductor has a value of 350 nanohenries ("nH"). The filter 1550 employs a capacitor C5 with a value of 5.2 nF and an inductor L9 with a value of 94 nH. Using these circuit components, the power amplifier operates along approximation curve 1710 in FIG. 17. As can be seen, the approximation curve 1710 closely approximates curve 1610 across a range of load impedances of approximately 1 to 3 ohms before beginning to deviate. Thus, the power supply 1510 is able to efficiently transfer power despite a 50% increase or decrease in load impedance from a midpoint load impedance of 2 ohms by varying a PWM duty cycle between 0.38 and 0.43.

Figure 18:
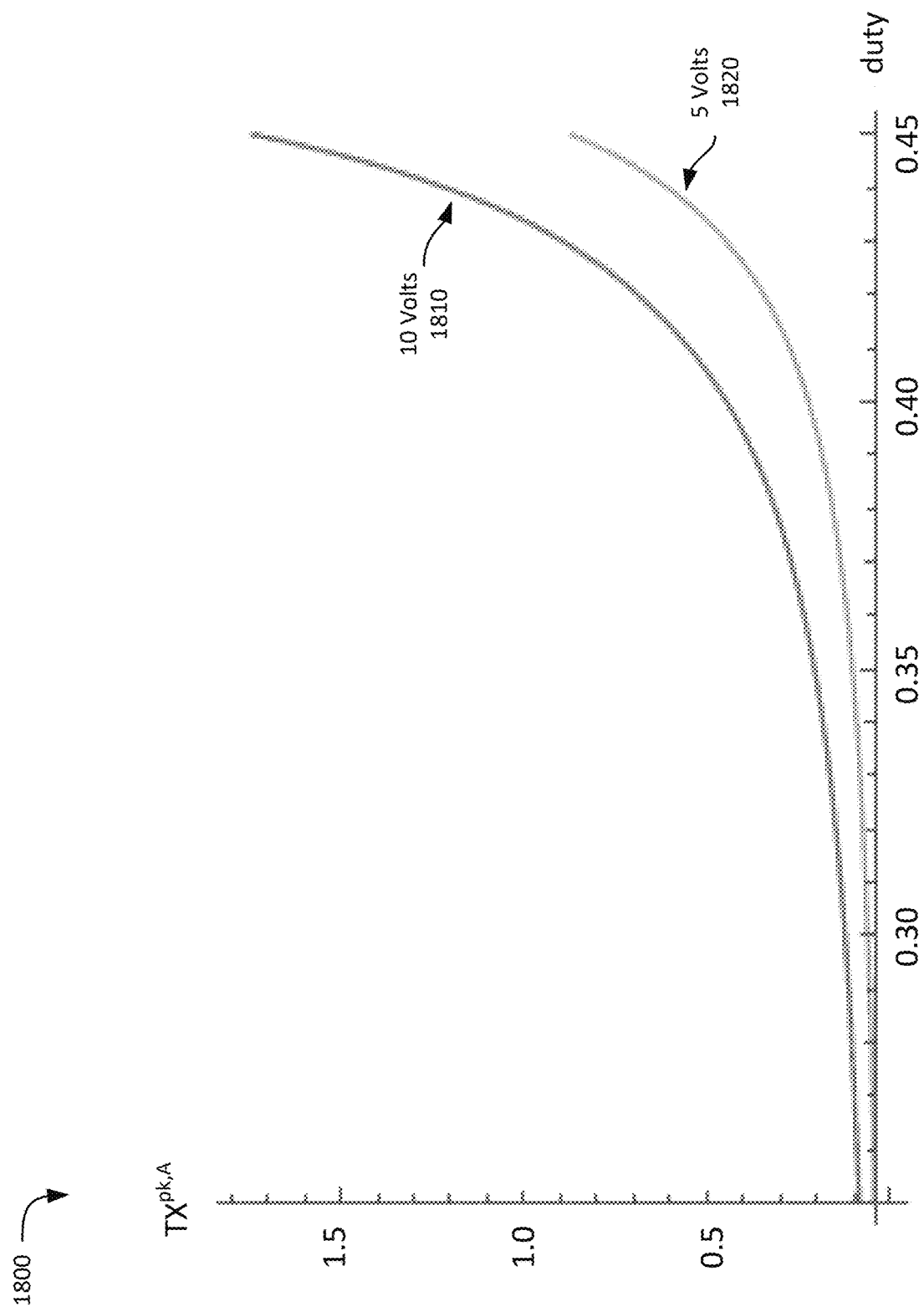
FIG. 18 shows a plot of power supply voltages to achieve a target current at a selected duty cycle.

Referring again to FIG. 15, in addition to adjusting a duty cycle setting for the PWM gate driver 1520, the controller 1570 adjusts the power supply 1510 output based on the PWM duty cycle. Referring to FIG. 18, FIG. 18 shows two curves 1810, 1820 representing current supplied to the transmit coil L7 (y-axis) by the power supply across a range of duty cycles (x-axis) at a particular voltage. In this example, the upper curve 1810 represents the output at 10 volts, while the lower curve 1820 represents the output at 5 volts. Thus, based on an amount of current to be supplied to the transmit coil L7, the voltage output by the DC/DC converter 1510 is adjusted based on the duty cycle. In this example, a decrease in the duty cycle corresponds to an increase in the voltage output by the DC/DC converter 1510. For example, to maintain a current of approximately 0.4 amps for change in the duty cycle from 0.43 to 0.39, the output of the DC/DC converter would increase from approximately 5 volts to approximately 10 volts. Thus FIG. 18 represents a portion of a three-dimensional surface, where the x-axis represents duty cycle, the y-axis represents transmit coil current, and the z-axis represents DC/DC converter output voltage. Using such a surface, a combination of duty cycle and current can be employed to select a DC/DC converter output voltage. Thus, in some examples, the lookup table may be a two-dimensional array.

Figure 19:
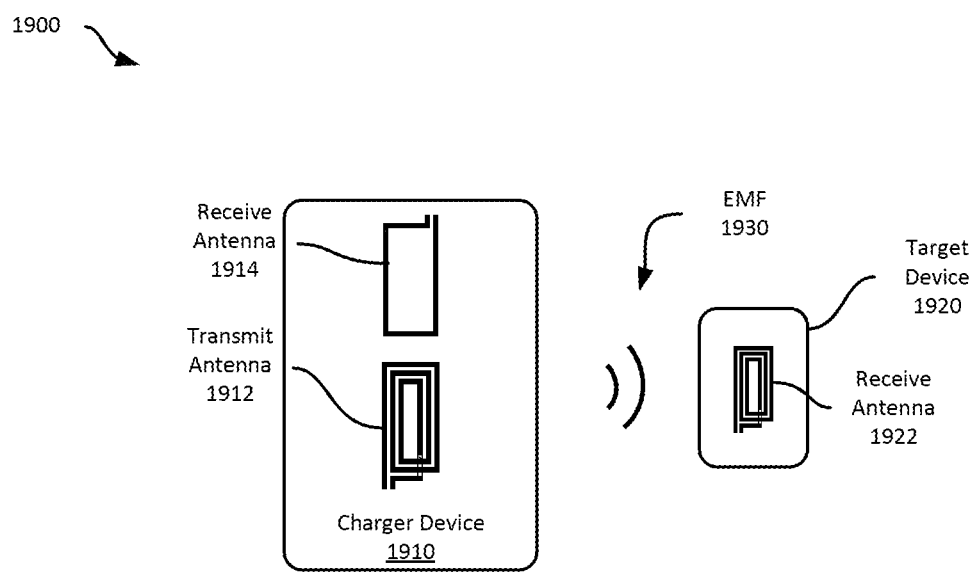
FIGS. 19-20 show example systems for dynamic control of near-field wireless power.

Referring now to FIG. 19, FIG. 19 shows an example system 1900 for dynamic control of near-field wireless power. Similar to the example shown in FIG. 11A, the system 1900 includes a charger device 1910 and a target device 1920. The charger device 1910 includes a transmit antenna coil 1912 and a receive antenna coil 1914; however, unlike the example shown in FIG. 11A, the two antenna coils 1912, 1914 in the charger device 1910 are not concentrically aligned. In this example, they are co-planar; however, in some examples, they may not be in the same plane, e.g., they may be positioned on opposite sides of a PCB. Thus, different arrangements of the transmit and receive coils 1912, 1914 may be used according to different examples.

Figure 20:
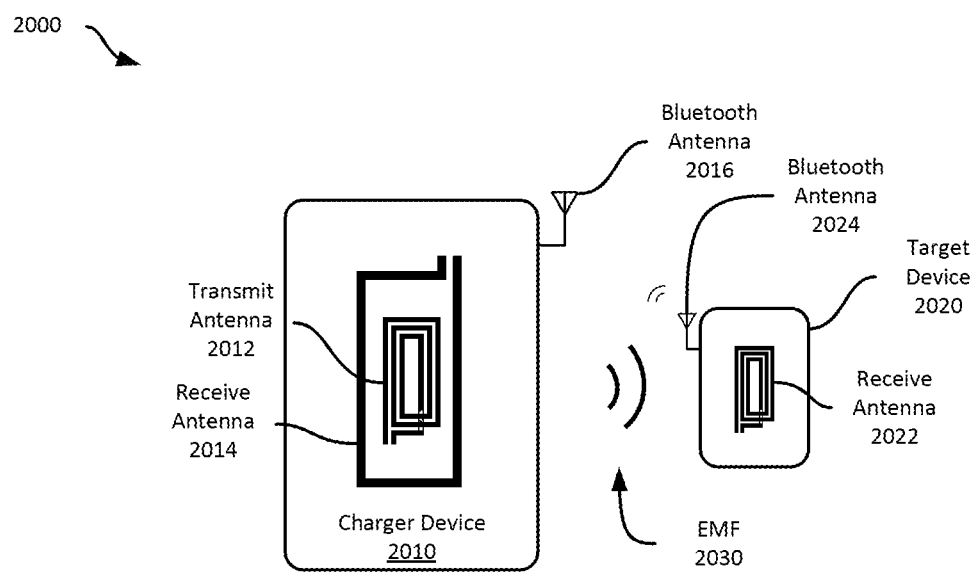

Referring now to FIG. 20, FIG. 20 shows another example system 2000 for dynamic control of near-field wireless power. In this example, the charger device 2010 and target device 2020 are similar to those shown in FIG. 11A, however, each also includes a Bluetooth ("BT") communications capabilities, e.g., BT low-energy ("BLE"). As discussed above, in some examples the target device 2020 can modify its apparent load impedance by activating and deactivating electronic components within the target device 2020. By doing so, it can communicate information to the charger device 2010, which will detect the changing load impedance as a change in phase of the generated EMF. In this example, however, the two devices 2010, 2020 may instead communicate such feedback information via a BT or BLE connection.

For example, the charger device 2010 may generate an EMF 2030 to provide electrical energy to the target device 2020, which may use that energy to power various components of the device, including the BT or BLE subsystem. The two devices may then pair using the BT or BLE communications technique and the target device 2020 may transmit feedback information, e.g., estimated received EMF strength, estimated power received, estimated power requirements, etc., to the charger device 2010. The charger device 2010 may then adjust the strength of the EMF 2030 based on such information, such as described above and as will be described below with respect to FIGS. 21-22.

Figure 21:
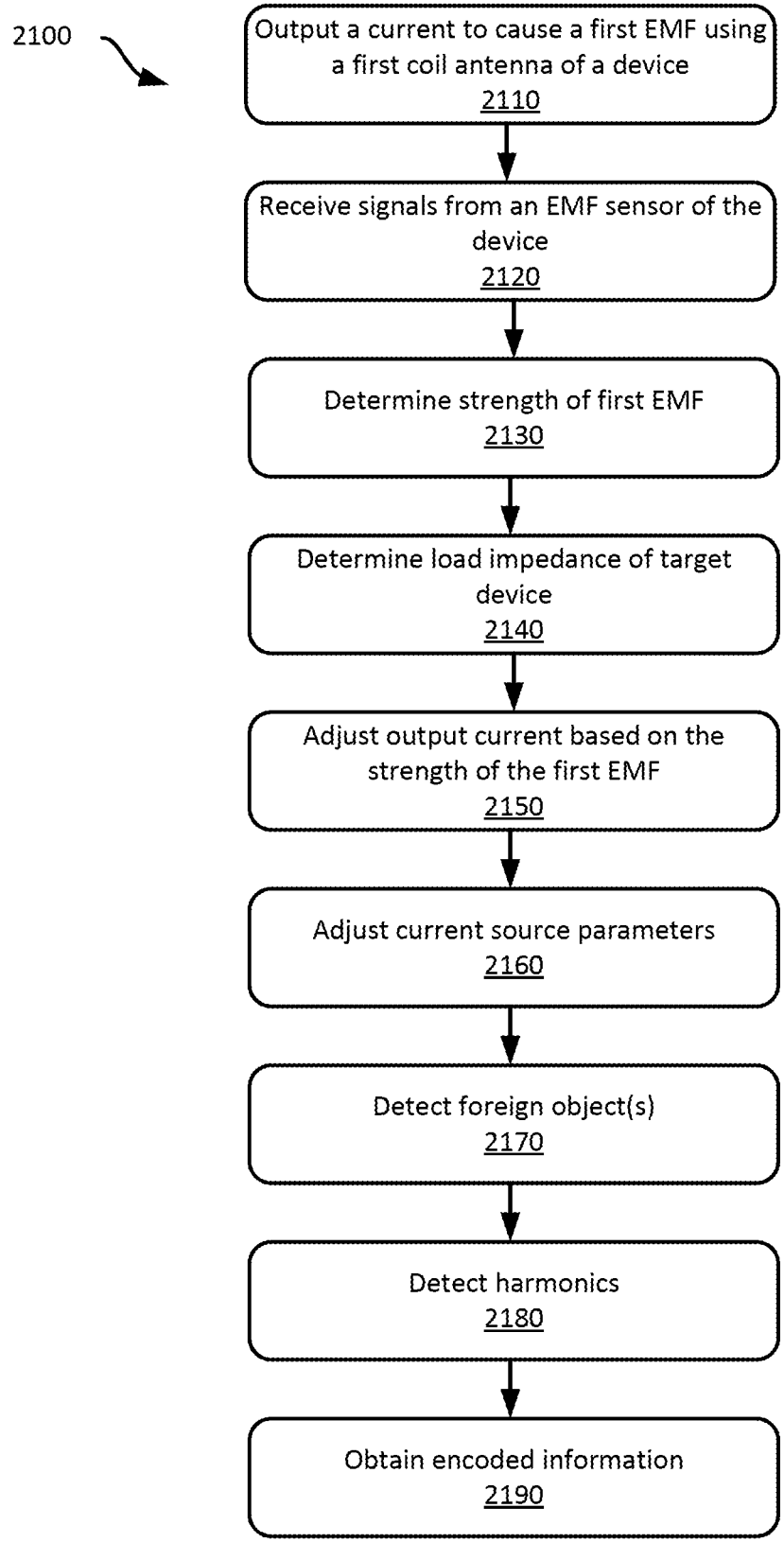
FIGS. 21-22 show example methods for dynamic control of near-field wireless power.

Referring now to FIG. 21, FIG. 21 shows an example method 2100 for dynamic control of near-field wireless power. This example method 2100 will be described with respect to the example device and technique shown in FIGS. 13-14. However, any suitable system, device, or technique according to this disclosure may be employed.

At block 2110, the charger device 1300 causes an electrical current source to output a current to the transmit antenna coil to generate an EMF. In this example, the processor 1310 outputs a signal to the current source 1322 to activate the current source 1322 to cause it to output an AC current to the transmit antenna coil 1324. The current source 1322 in this example is a switching power amplifier, such as the example shown in FIG. 15. The current source 1322 outputs the AC current at a predetermined frequency and with a predetermined default amount of current.

At block 2120, the processor 1310 receives one or more signals from the EMF sensor 1330. In this example, the processor 1310 receives a magnitude signal from the peak detector 1333 that indicates a peak magnitude of a received EMF. As discussed above the EMF sensor 1330 employs a receive antenna coil 1331 to receive electrical energy from the EMF generated by the wireless field driver 1320. The received electrical energy is then communicated to the peak detector 1333. The peak detector 1333 receives the signal from the receive antenna coil 1331 and outputs a signal indicating the maximum amplitude of the received EMF. It should be appreciated that the signal output by the peak detector in this example is an analog voltage signal, in some examples, the peak detector 1333 may output a digital value indicating the maximum amplitude of the received EMF. For example, the peak detector 1333 may employ an analog to digital converter to generate a digital representation of the maximum amplitude. The output of the peak detector 1333 in some examples may be a DC signal, though it should be appreciated that the signal may change based on the strength of the EMF.

In addition to the magnitude signal, in this example the processor 1310 also receives a phase signal from the phase detector 1337. The phase signal indicates a difference in phase between the received EMF and a reference signal 1339. In this example, the reference signal 1339 is output at the same frequency and phase as the AC current output by the current source 1322. In some examples, the reference signal 1339 may be output by the current source 1322. As discussed above, the phase detector 1337 receives a signal from the zero-crossing detector 1335, e.g., a square wave, and a reference signal. If the reference signal 1339 is output by the current source 1322, it may be converted into a square wave, if it is not initially output as one. Any phase shift in the received EMF will result in periods during which the voltages (or currents) of the two signals are not equal. The duration of these differences with respect to the frequency of the two signals indicates the amount of phase shift. The phase detector 1337 detects these differences in values, e.g., using a comparator, and outputs a signal indicating the phase difference to the processor 1310.

It should be appreciated that the phase detection functionality may be omitted in some examples. While phase information can be used for a variety of functionality, it may not be necessary to estimate the strength of the generated EMF and so may be omitted.

At block 2130, the processor 1310 determines a strength of the generated EMF. In this example, the processor 1310 receives the magnitude signal from the peak detector 1333 and determines the strength of the generated EMF based on the magnitude signal. In this example, the processor 1310 employs a lookup table that correlates peak signal values, e.g., voltage, with EMF strength. However, in some examples, the processor 1310 may calculate an estimated EMF strength based on the magnitude signal and a characterization of the wireless field generator, e.g., based on transmit antenna coil (e.g., number of turns), and an amount of current output by the current source 1222, using Faraday's law.

At block 2140, the processor 1310 determines a load impedance of the target device. In this example, the processor 1310 determines the load impedance of the target device based on the phase difference output by the phase detector 1337. In this example, the processor 1310 employs a lookup table that associates phase shifts with load impedances.

At block 2150, the processor 1310 adjusts the current source to adjust an amount of current output by the wireless field driver to adjust the strength of the generated EMF. For example, the processor 1310 may adjust the amount of current to maintain a power characteristic of the generated EMF based on feedback information from the EMF sensor 1330. Such a power characteristic may be an amplitude of the generated EMF, a frequency of the generated EMF, a phase of the generated EMF, etc. Such power characteristics may further be maintained or adjusted based on load impedance measurements, changes in power requirements for a remote device, etc. For example, as discussed above with respect to FIG. 14, the processor 1310 may implement a PID controller (or other feedback control system) to adjust the output current of the wireless field driver 1320.

At block 2160, the processor 1310 adjusts operational parameters for the current source. In this example, the charger device 1300 employs a tunable switching power amplifier, such as the one depicted in FIG. 15. To adjust the operational parameters, the processor 1310 may adjust the output voltage of the DC power supply or a duty cycle of the PWM gate driver 1520 based on the load impedance estimated at block 2140 as discussed above with respect to FIGS. 15-17.

In some examples the processor 1310 may adjust an output voltage or a duty cycle of the power amplifier to reduce power consumption. For example, the processor 1310 may cause the current source to output a constant current while adjusting the duty cycle of the PWM gate driver. The amount of power consumed by the current source may then be measured and provided to the processor 1310. The processor 1310 may then vary the duty cycle across a range of values and determine a duty cycle that has a minimum power consumption for the tested duty cycles.

At block 2170, the processor 1310 may detect one or more foreign objects. In one example, the processor 1310 may compare the estimated load impedance against one or more threshold values to determine if the load impedance is within an expected range, or above (or below) an expected value. If the estimated load impedance falls outside of the expected range or does not meet the expected threshold, the processor 1310 may determine that a foreign object is present and interfering with the generated EMF.

At block 2180, the processor 1310 may determine one or more voltage or current harmonics within the generated EMF. For example, the processor 1310 may implement a fast-Fourier transform to obtain a spectral representation of the EMF. The processor 1310 may then identify one or more peak frequencies within the spectral representation to identify one or more harmonics. Alternatively, the processor 1310 may implement, or may be in communication with, one or more bandpass filters set to isolate one or more pre-determined frequencies. The processor 1310 may then determine a strength of the signals output by the filter(s) and compare the strength of the signals to one or more thresholds to determine if a harmonic frequency is present. If one or more harmonics is detected, it may indicate that the charger device 1300 is causing harmful interference. Thus, the processor 1310 may reduce the strength of the generated EMF until the strength of the detected harmonics falls below a predetermined threshold. To reduce the strength of the generated EMF, the processor 1310 may implement a second PID controller (or other suitable feedback controller), similar to the example shown in FIG. 15; however, the error signal may be the strength of the harmonic(s) and the target signal may be the threshold maximum tolerable harmonic strength.

It should be appreciated that some harmonics, e.g., high-frequency harmonics in the gigahertz range, may not be measured directly. Instead, the processor may indirectly detect such harmonics based on the presence of lower-frequency harmonics, e.g., in the sub-100 MHz range. The processor may then determine an estimated magnitude of one or more high-frequency harmonics, or determine whether an estimated magnitude of the high-frequency harmonics likely exceed a threshold magnitude, e.g., based on the magnitude of the lower-frequency harmonics exceeding a threshold.

In addition, the processor may detect whether such harmonics are present, e.g., by detecting a threshold power level at one or more predetermined harmonic frequencies, and then, based on a lack of such harmonics in conjunction with a threshold amount of phase shift, may determine that a foreign object is present, as a continuation of the functionality discussed above with respect to block 2170.

At block 2190, the processor 1310 may obtain information output by the target device. For example, as discussed above, the target device may modulate its load impedance by activating and deactivating electronic functionality to transmit digital data via the generated EMF. Such changes in load impedance may be detected by the phase detector 1337. By detecting changes between two different load impedances, the processor 1310 may detect binary values output at a pre-determined bit rate. For example, if the target device modulates its load impedance once per millisecond, the processor 1310 may sample the phase information once per millisecond to obtain a single bit. For example, if the phase shifts between two values, one value may represent a binary "1" and the other may represent a binary "0." Thus, the processor 1310 may obtain a series of such binary values to obtain feedback information from the target device, e.g., an expected power requirement, a battery power level, etc.

While the method of FIG. 21 was described as including certain features being performed in a particular order, it should be appreciated that any of blocks 2130-2190 may be performed in any suitable order. For example, the processor 1310 may determine load impedance at block 2140 before determining the strength of the EMF. Similarly, one or more blocks shown in FIG. 21 are option. For example, one or more of blocks 2140 and 2160-2190 may be omitted in some examples. In some examples, blocks 2130 and 2150 may be omitted. Thus, different examples methods may provide different functionality relating to control of the EMF, information about the status of a target device, information about nearby foreign objects, or harmful EMI.

Figure 22:
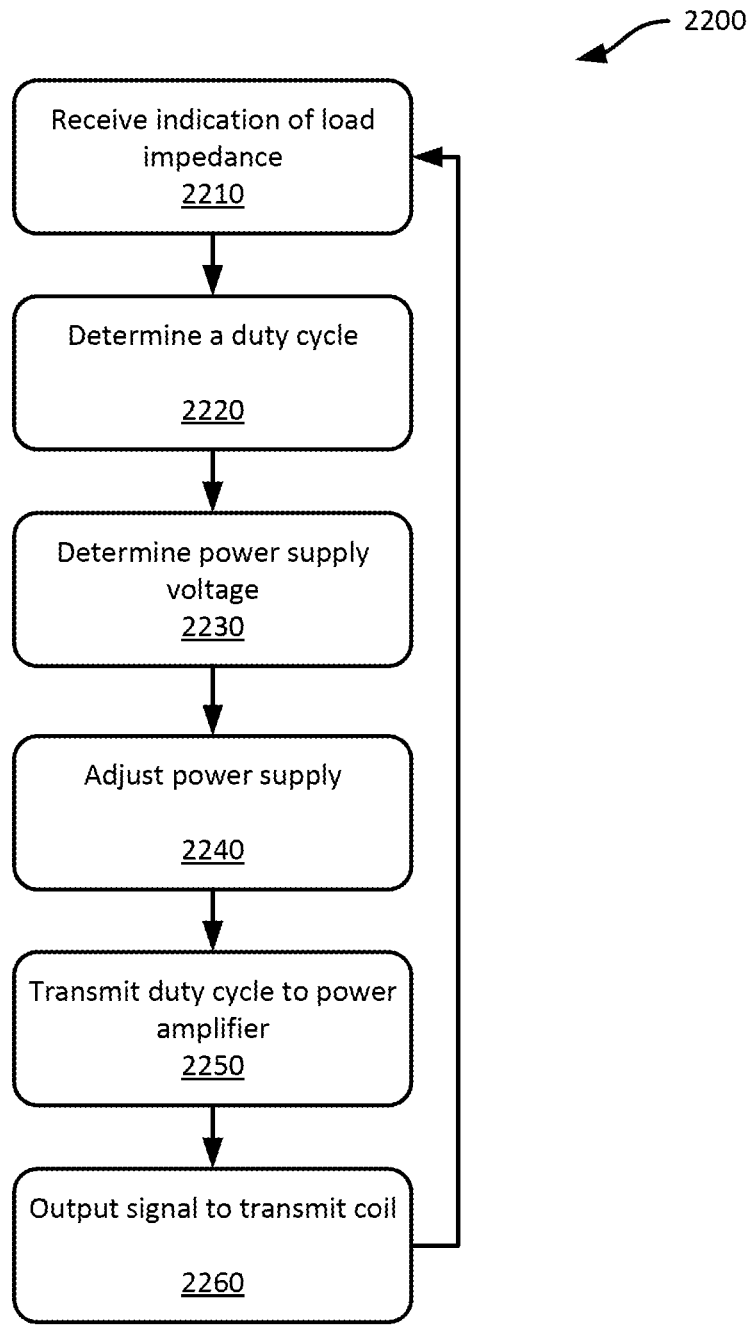

Referring now to FIG. 22, FIG. 22 provides a method for controlling a power amplifier, such as a power amplifier shown in FIG. 15. Though it should be appreciated that any suitable power amplifier may be employed.

At block 2210, the controller 1570 receives an indication of load impedance from the impedance sensor 2260. In this example, the controller 1570 receives a voltage signal from the impedance sensor 2260 corresponding to a load impedance. However, in some examples, the controller 1570 may receive a current signal, PWM signal, or a digital value indicating a load impedance. Still any other suitable impedance sensor may be employed.

At block 2220, the controller 1570 determines a duty cycle based on the load impedance. In this example, the controller 1570 accesses a look-up table stored in memory and determines a duty cycle corresponding to the load impedance. However, in some examples, the controller 1570 may determine a duty cycle based on the load impedance and a mapping function stored in memory. For example a mapping function may comprise one or more polynomial functions mapping load impedance to duty cycle, such as described above with respect to FIGS. 11A-11B.

At block 2230, the controller 1570 determines a power supply voltage based on the determined duty cycle. In this example, the controller 1570 accesses a look-up table and determines a power supply voltage corresponding to the determined duty cycle. However, in some examples, the controller may determine a power supply voltage based on the duty cycle and a mapping function. For example a mapping function may comprise one or more polynomial functions mapping duty cycle to power supply voltage, such as described above with respect to FIGS. 11A-11B.

At block 2240, the controller 1570 transmits a signal to the DC/DC converter 1510 to adjust its output voltage based on the determined power supply voltage. In this example, the signal is a voltage signal indicating the determined power supply voltage; however, any suitable signal may be provided, including a current signal, a digital value indicating an output voltage selection, a PWM signal, etc.

At block 2250, the controller 1570 transmits the determined duty cycle to the power amplifier 1530. In this example, the controller 1570 transmits a voltage signal to a PWM gate controller, such as the PWM gate controller 1520, to establish the determined duty cycle. Other suitable signals may be employed according to different examples, such as current signals, digital values, etc. In some examples, the controller comprises a processor having an integrated PWM circuit, and thus, the controller 1570 may adjust an output duty cycle of the PWM circuit to provide a PWM signal.

At block 2260, the power amplifier 1530 outputs a power signal to the transmit coil L7 using the impedance transformation network 1550 based on the determined duty cycle.

It should be appreciated that while the method 2200 of FIG. 22 is described in a particular order, other orderings may be possible. For example, blocks 2240 and 2250 may be reversed according to some examples, or may occur substantially simultaneously.

Figure 23:
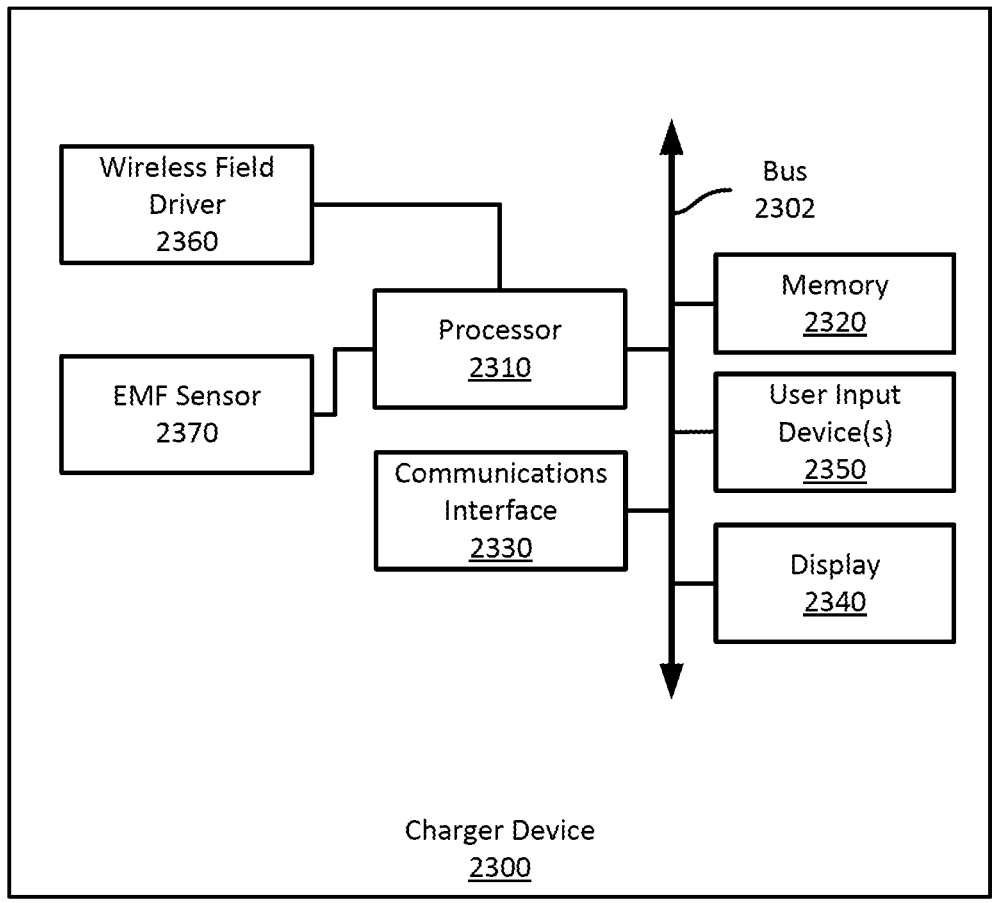
FIG. 23 shows an example computing device suitable for dynamic control near-field wireless power.

Referring now to FIG. 23, FIG. 23 shows an example charger device 2300 suitable for use in example systems or methods for dynamic control of near-field wireless power according to this disclosure. The example computing device 2300 includes a processor 2310 which is in communication with the memory 2320 and other components of the computing device 2300 using one or more communications buses 2302. The processor 2310 is configured to execute processor-executable instructions stored in the memory 2320 to perform one or more methods for dynamic control of near-field wireless power according to different examples, such as part or all of the example methods 1000 and 2200 described above with respect to FIGS. 21-23. The computing device, in this example, also includes one or more user input devices 2350, such as a keyboard, mouse, touchscreen, microphone, buttons, etc., to accept user input. The computing device 2300 also includes a display 2340 to provide visual output to a user. Further, as discussed above with respect to FIGS. 11A, 11B, and 3, the charger device 2300 also includes a wireless field driver 2360 and an EMF sensor 2370.

The computing device 2300 also includes a communications interface 2330. In some examples, the communications interface 2330 may enable communications using one or more communication techniques, such as BT or BLE, or using one or more communication networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A device comprising:
    a wireless field driver comprising a first antenna coil and an electrical current source electrically coupled to the first antenna coil, the electrical current source comprising a DC/DC converter, a pulse-width modulation ("PWM") gate controller, and a switching power amplifier;
    an electromagnetic field ("EMF") sensor comprising a second antenna coil and a phase detector, wherein the EMF sensor is configured to generate a sensor signal indicative of a signal strength from the first antenna coil and a phase signal indicate a phase change;
    a non-transitory computer-readable medium; and
    a processor in communication with the non-transitory computer-readable medium, the processor configured to execute processor-executable instructions stored in the non-transitory computer-readable medium to:
        cause the electrical current source to output a current to the first antenna coil to generate a first EMF;
        estimate the signal strength of the first EMF based on the sensor signal;
        determine a change in load impedance based on the phase signal; and
        adjust a duty cycle of the PWM gate controller and a voltage output by the DC/DC converter to adjust the current to the first antenna coil based on an estimated signal strength of the first EMF and the change in load impedance to maintain a power characteristic and generate a second EMF at the first antenna coil to charge a wearable device.

2. The device of claim 1, wherein the first and second antenna coils are positioned concentrically with respect to each other, the second antenna coil having a greater width than the first antenna coil.

3. The device of claim 2, wherein the first and second antenna coils are co-planar with respect to each other.

4. The device of claim 1, wherein the processor is further configured to execute processor-executable instructions stored in the non-transitory computer-readable medium to determine a presence of a foreign object based on the signal received from the EMF sensor.

5. The device of claim 1, wherein the processor is further configured to execute processor-executable instructions stored in the non-transitory computer-readable medium to determine one or more harmonic frequencies based on the signal received from the EMF sensor.

6. The device of claim 1, wherein the EMF sensor further comprises a peak detector and the one or more signals received from the EMF sensor comprises an amplitude signal output by the peak detector, and wherein the processor is further configured to execute processor-executable instructions stored in the non-transitory computer-readable medium to determine the strength of the first EMF based on the amplitude signal.

7. The device of claim 1, wherein the EMF sensor further comprises a zero-crossing detector, and wherein the processor is further configured to execute processor-executable instructions stored in the non-transitory computer-readable medium to:
    determine the strength of the first EMF based on the phase signal.

8. The device of claim 1, further comprising a power sensor electrically coupled to the wireless field driver, and wherein the processor is further configured to execute processor-executable instructions stored in the non-transitory computer-readable medium to:
    vary switching frequencies of the electrical current source;
    maintain a substantially constant strength of the first EMF based on the one or more signals received from the EMF sensor;
    receive power signals from the power sensor corresponding to the varied switching frequencies, the power signals indicating the power output by the switching power amplifier at the varied switching frequencies; and
    establish an efficient switching frequency of the switching power amplifier based on the varied switching frequencies and corresponding power output by the switching power amplifier at the varied switching frequencies.

9. A method comprising:
    causing an electrical current source of a wireless field driver of a wireless device to output a current to a first antenna coil to generate a first EMF, the electrical current source comprising a DC/DC converter, a pulse-width modulation ("PWM") gate controller, and a switching power amplifier;
    receiving one or more signals from an EMF sensor of the wireless device indicating a sensed strength of the first EMF and a phase change, the EMF sensor comprising a second antenna coil;
    estimating a strength of the first EMF based on the one or more sensor signals;
    determine a change in load impedance based on the phase change; and
    adjusting, by a processor, a duty cycle of the PWM gate controller and a voltage output by the DC/DC converter to adjust the current based on the estimated strength of the first EMF and the phase change to generate a second EMF at the first antenna coil to charge another electronic device.

10. The method of claim 9, wherein the first and second antenna coils are positioned concentrically with respect to each other, the second antenna coil having a greater width than the first antenna coil.

11. The method of claim 9, wherein the first and second antenna coils are co-planar with respect to each other.

12. The method of claim 9, further comprising determining a presence of a foreign object based on the signal received from the EMF sensor.

13. The method of claim 9, further comprising determining one or more harmonic frequencies based on the signal received from the EMF sensor.

14. The method of claim 9, wherein the EMF sensor further comprises a peak detector and the one or more signals received from the EMF sensor comprises an amplitude signal output by the peak detector, and further comprising determining the strength of the first EMF based on the amplitude signal.

15. The method of claim 9, wherein the EMF sensor further comprises a zero-crossing detector, and further comprising:
   determining the strength of the first EMF based on the phase signal.

16. The method of claim 9, wherein the wireless device further comprises a power sensor electrically coupled to the wireless field driver, and further comprising:
   varying switching frequencies of the electrical current source;
   maintaining a substantially constant strength of the first EMF based on the one or more signals received from the EMF sensor;
   receiving power signals from the power sensor corresponding to the varied switching frequencies, the power signals indicating the power output by the switching power amplifier at the varied switching frequencies; and
   establishing an efficient switching frequency of the switching power amplifier based on the varied switching frequencies and corresponding power output by the switching power amplifier at the varied switching frequencies.

17. A non-transitory computer-readable medium comprising processor-executable instructions to cause a processor to:
   cause an electrical current source of a wireless field driver of a wireless device to output a current to a first antenna coil to generate a first EMF, the electrical current source comprising a DC/DC converter, a pulse-width modulation ("PWM") gate controller, and a switching power amplifier;
   receive one or more signals from an electromagnetic field ("EMF") sensor indicating a sensed strength of the first EMF and a phase change, the EMF sensor comprising a second antenna coil;
   determine a strength of the first EMF based on the one or more signals;
   determine a change in load impedance based on the phase change; and
   adjust a duty cycle of the PWM gate controller and a voltage output by the DC/DC converter to adjust the current based on the sensed strength of the first EMF and the phase change to generate a second EMF to charge another electronic device.

18. The non-transitory computer-readable medium of claim 17, further comprising processor-executable instructions configured to cause the processor to determine a presence of a foreign object based on the signal received from the EMF sensor.

19. The non-transitory computer-readable medium of claim 17, further comprising processor-executable instructions configured to cause the processor to determine one or more harmonic frequencies based on the signal received from the EMF sensor.

20. The non-transitory computer-readable medium of claim 17, wherein the EMF sensor further comprises a peak detector and the one or more signals received from the EMF sensor comprises an amplitude signal output by the peak detector, and further comprising processor-executable instructions configured to cause the processor to determine the strength of the first EMF based on the amplitude signal.

21. The non-transitory computer-readable medium of claim 17, wherein the EMF sensor further comprises a zero-crossing detector, and further comprising processor-executable instructions configured to cause the processor to:
   determine the strength of the first EMF based on the phase signal.

22. The non-transitory computer-readable medium of claim 17, wherein the wireless device comprises a power sensor electrically coupled to the wireless field driver, and further comprising processor-executable instructions configured to cause the processor to:
   vary switching frequencies of the electrical current source;
   maintain a substantially constant strength of the first EMF based on the one or more signals received from the EMF sensor;
   receive power signals from the power sensor corresponding to the varied switching frequencies, the power signals indicating the power output by the switching power amplifier at the varied switching frequencies; and
   establish an efficient switching frequency of the switching power amplifier based on the varied switching frequencies and corresponding power output by the switching power amplifier at the varied switching frequencies.

* * * * *